(12) United States Patent
Abramovich et al.

(10) Patent No.: US 11,471,117 B2
(45) Date of Patent: Oct. 18, 2022

(54) MULTIPOSITION COLLIMATION DEVICE AND X-RAY IMAGING SYSTEMS

(71) Applicant: DENTSPLY SIRONA Inc., York, PA (US)

(72) Inventors: Mark Abramovich, Brooklyn, NY (US); Aaron Bratslavsky, Brooklyn, NY (US); Charles Smith, Brooklyn, NY (US); Stan Mandelkern, Teaneck, NY (US); Liang Hwang, Millstone, NJ (US)

(73) Assignee: Dentsply Sirona Inc., York, PA (US)

( * ) Notice: Subject to any disclaimer, the term of this patent is extended or adjusted under 35 U.S.C. 154(b) by 0 days.

(21) Appl. No.: 15/463,325

(22) Filed: Mar. 20, 2017

(65) Prior Publication Data

US 2018/0263578 A1    Sep. 20, 2018

(51) Int. Cl.
```
A61B 6/06     (2006.01)
A61B 6/14     (2006.01)
A61B 6/00     (2006.01)
A61B 6/02     (2006.01)
A61B 6/08     (2006.01)
G21K 1/02     (2006.01)
```

(52) U.S. Cl.
CPC ............. *A61B 6/06* (2013.01); *A61B 6/025* (2013.01); *A61B 6/08* (2013.01); *A61B 6/14* (2013.01); *A61B 6/145* (2013.01); *A61B 6/42* (2013.01); *A61B 6/4429* (2013.01); *A61B 6/4452* (2013.01); *A61B 6/547* (2013.01); *A61B 6/587* (2013.01); *G21K 1/02* (2013.01)

(58) Field of Classification Search
CPC .. A61B 6/14; A61B 6/145; A61B 6/06; A61B 6/08; A61B 6/42; A61B 6/4429; A61B 6/547; A61B 6/587; G21K 1/02
See application file for complete search history.

(56) References Cited

U.S. PATENT DOCUMENTS 4,223,228 A * 9/1980 Kaplan ................. A61B 6/145
                                                    324/207.2
4,554,676 A * 11/1985 Maldonado .......... G03B 42/042
                                                      378/170

(Continued)

FOREIGN PATENT DOCUMENTS

WO    2017/196413 A1    11/2017

OTHER PUBLICATIONS

International Search Report and Written Opinion of the International Searching Authority in International Patent Application No. PCT/US2018/023345, dated Jul. 27, 2018.

(Continued)

*Primary Examiner* — David J Makiya
*Assistant Examiner* — Soorena Kefayati
(74) *Attorney, Agent, or Firm* — Venable LLP

(57) ABSTRACT

Multiposition collimation devices and x-ray imaging systems, which include the multiposition collimation devices, are provided. The multiposition collimation device includes a collimator housing and a collimator plate constructed to at least partially block the passage of x-rays. The collimator plate is movable relative to the collimator housing to a first position, corresponding to a first x-ray detector size, and a second position, corresponding to a second x-ray detector size.

20 Claims, 21 Drawing Sheets

(56) References Cited

U.S. PATENT DOCUMENTS

| | | | | |
|---|---|---|---|---|
| 4,937,849 | A * | 6/1990 | Hubert | A61B 6/06 378/150 |
| 5,406,611 | A * | 4/1995 | Schobert | A61N 5/10 378/150 |
| 5,463,669 | A * | 10/1995 | Kaplan | A61B 6/08 378/170 |
| 6,343,875 | B1 * | 2/2002 | Eppinger | A61B 6/4435 378/170 |
| 9,144,410 | B1 * | 9/2015 | Chen | A61B 6/145 |
| 2003/0012331 | A1 * | 1/2003 | Kojima | A61B 6/037 378/4 |
| 2003/0161438 | A1 * | 8/2003 | Woods | A61B 6/501 378/19 |
| 2007/0223649 | A1 * | 9/2007 | De Godzinsky | A61B 6/145 378/4 |
| 2008/0118023 | A1 * | 5/2008 | Besson | A61B 6/4216 604/510 |
| 2008/0298543 | A1 * | 12/2008 | Razzano | A61B 6/4411 378/170 |
| 2009/0135508 | A1 * | 5/2009 | Matozaki | G11B 7/1376 359/823 |
| 2009/0220053 | A1 * | 9/2009 | Tresso | A61C 19/02 378/189 |
| 2010/0254510 | A1 * | 10/2010 | Yoon | A61B 6/4233 378/37 |
| 2012/0039445 | A1 * | 2/2012 | Kantor | G21K 1/02 378/147 |
| 2012/0093284 | A1 * | 4/2012 | Takemoto | A61B 6/027 378/19 |
| 2013/0136238 | A1 * | 5/2013 | Laws | G21K 1/046 378/147 |
| 2013/0251109 | A1 * | 9/2013 | Becca | G21K 1/04 378/150 |
| 2014/0010349 | A1 * | 1/2014 | De Godzinsky | A61B 6/588 378/62 |
| 2014/0010350 | A1 * | 1/2014 | De Godzinsky | A61B 6/14 378/62 |
| 2014/0147001 | A1 * | 5/2014 | Jouhikainen | A61B 6/14 382/103 |
| 2014/0161234 | A1 * | 6/2014 | Razzano | A61B 6/14 378/147 |
| 2014/0169533 | A1 * | 6/2014 | Razzano | A61B 6/14 378/205 |
| 2014/0226793 | A1 * | 8/2014 | Elvin | A61B 6/469 378/150 |
| 2014/0270068 | A1 * | 9/2014 | Hayman | A61B 6/06 378/62 |
| 2015/0004558 | A1 * | 1/2015 | Inglese | A61B 6/5235 433/29 |
| 2015/0359504 | A1 * | 12/2015 | Zhou | A61B 6/587 378/38 |
| 2015/0374315 | A1 * | 12/2015 | Hayman | A61B 6/14 378/153 |
| 2016/0038105 | A1 * | 2/2016 | Hayman | A61B 6/4435 378/150 |
| 2016/0051211 | A1 * | 2/2016 | Linev | A61B 6/4014 378/62 |
| 2016/0270745 | A1 * | 9/2016 | Heath | A61B 6/4007 |
| 2016/0287198 | A1 * | 10/2016 | Abramovich | A61B 6/105 |
| 2017/0287581 | A1 * | 10/2017 | Righini | G21K 1/025 |
| 2017/0311909 | A1 * | 11/2017 | Congy | G21K 1/02 |
| 2018/0292333 | A1 * | 10/2018 | Chen | G01N 23/083 |

OTHER PUBLICATIONS

Nov. 10, 2020 Communication in European Patent Application No. 18 716 749.9.

* cited by examiner

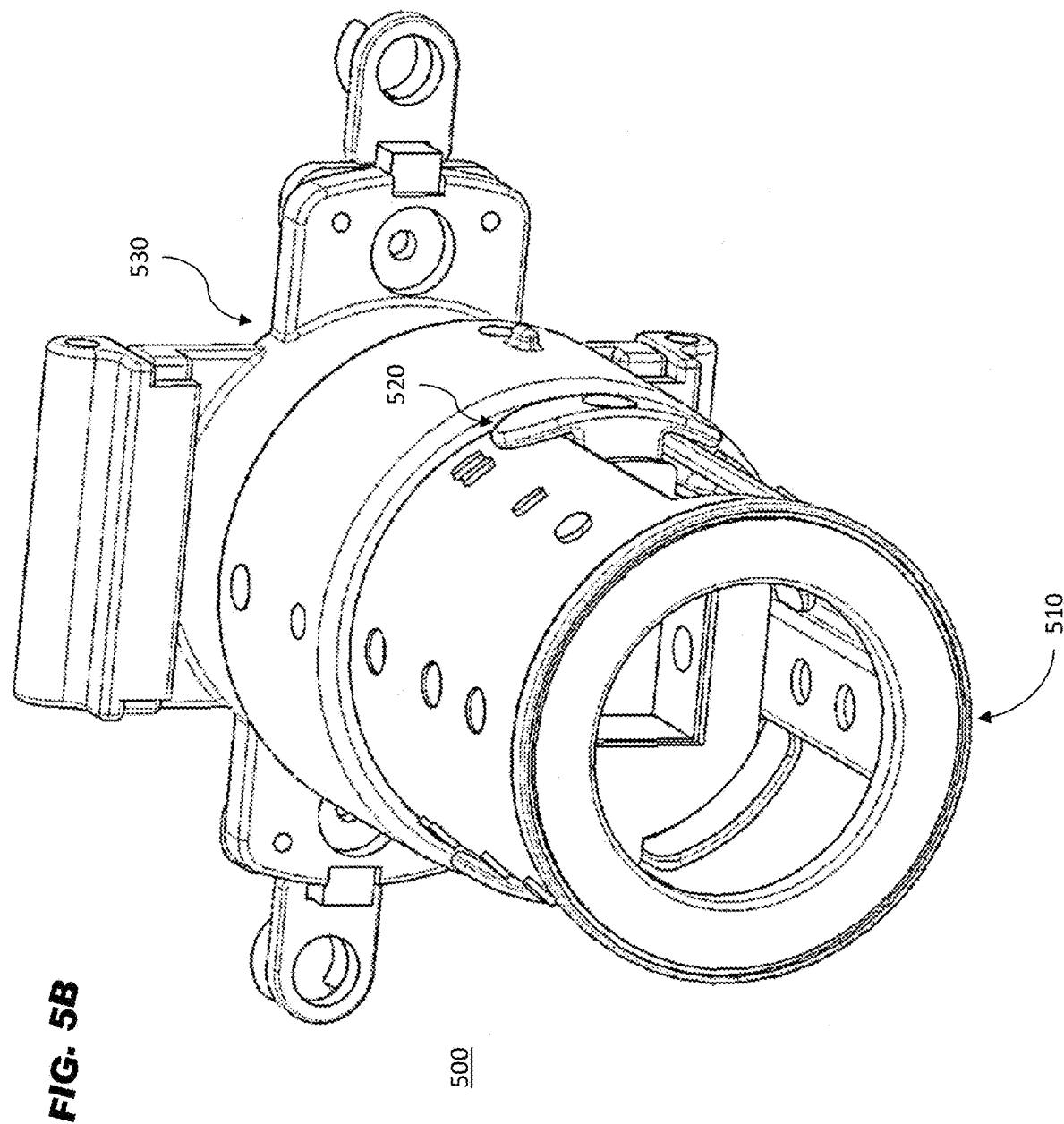

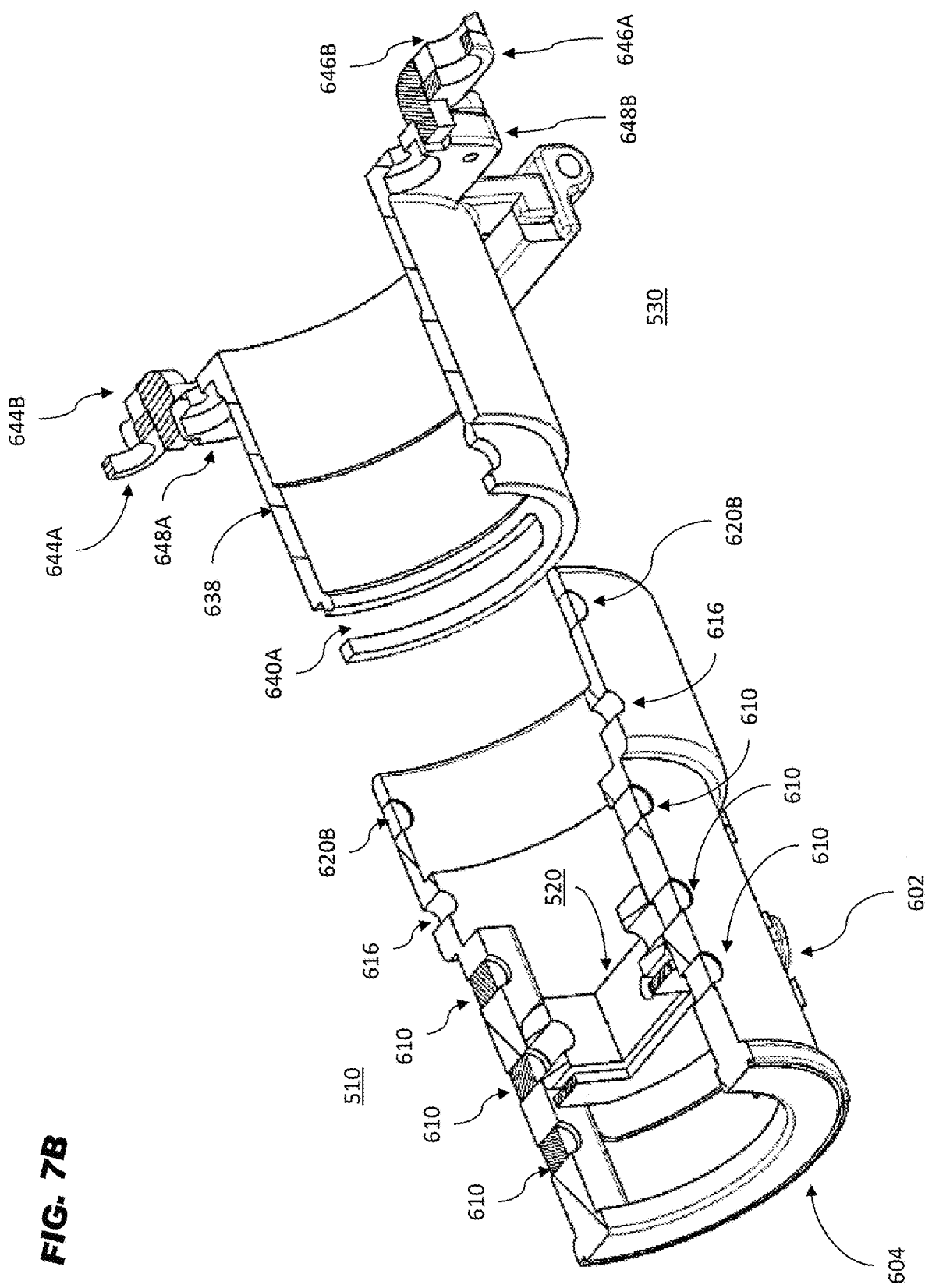

MULTIPOSITION COLLIMATION DEVICE AND X-RAY IMAGING SYSTEMS

BACKGROUND

Field of the Invention

The present application relates generally to a multiposition collimation device for an x-ray source and x-ray imaging systems that use the multiposition collimation device.

Description of Related Art

X-ray radiography can be performed by positioning an x-ray source on one side of an object (e.g., a patient or a portion thereof) and emitting x-rays from that source, through the object, and toward an x-ray detector (e.g., radiographic film, an electronic digital detector, or a photostimulable phosphor plate) located on the other side of the object. As the x-rays pass through the object they are attenuated to varying degrees depending on the composition of the object. X-rays arriving at the x-ray detector form a two-dimensional (2D) x-ray image (also known as a radiograph) based on the cumulative absorption through the object.

Tomosynthesis provides three-dimensional information about a patient in the form of tomographic image slices reconstructed from x-ray images of the patient taken from multiple perspectives within a scan angle smaller than that of computed tomography (CT) or cone-beam computed tomography (CBCT) (e.g., ±20°, compared with at least 180° in CBCT).

In order to limit x-ray exposure to only those areas of diagnostic inquiry, it is beneficial to collimate the x-ray beam so that only the patient's volume of interest (the region of space relevant to the diagnostic inquiry) is radiated. It is also beneficial to ensure that the x-ray source is correctly positioned and aligned with respect to the x-ray detector. Therefore, it would be desirable to have a collimation device which could provide beneficial collimation and aid in the positioning and alignment during a tomosynthesis imaging operation.

SUMMARY OF THE INVENTION

One or more the above limitations may be diminished by collimation devices and x-ray imaging systems described herein.

In one embodiment, a collimation device for a dental imaging apparatus is provided. The collimation device includes a collimator housing and a collimator plate constructed to at least partially block the passage of x-rays. The collimator plate is movable relative to the collimator housing to a first position, corresponding to a first x-ray detector size, and a second position, corresponding to a second x-ray detector size.

In another embodiment, an x-ray imaging system is provided. The x-ray imaging system includes an x-ray source, configured to generate an x-ray beam, and a collimation device. The collimation device is connected to the x-ray source and includes: a collimator housing and a collimator plate. The collimator plate is constructed to at least partially block the passage of x-rays. The collimator plate is movable relative to the collimator housing to a first position, corresponding to a first x-ray detector size, and a second position, corresponding to a second x-ray detector size. The collimation device is arranged to receive the x-ray beam generated by the x-ray source.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5B is a perspective view of a collimation device according to one embodiment of the present invention in a vertical position;

FIGS. 7A-C are sectional views of a collimation device showing a collimator mount assembly at three different positions according to one embodiment;

Figure 1:
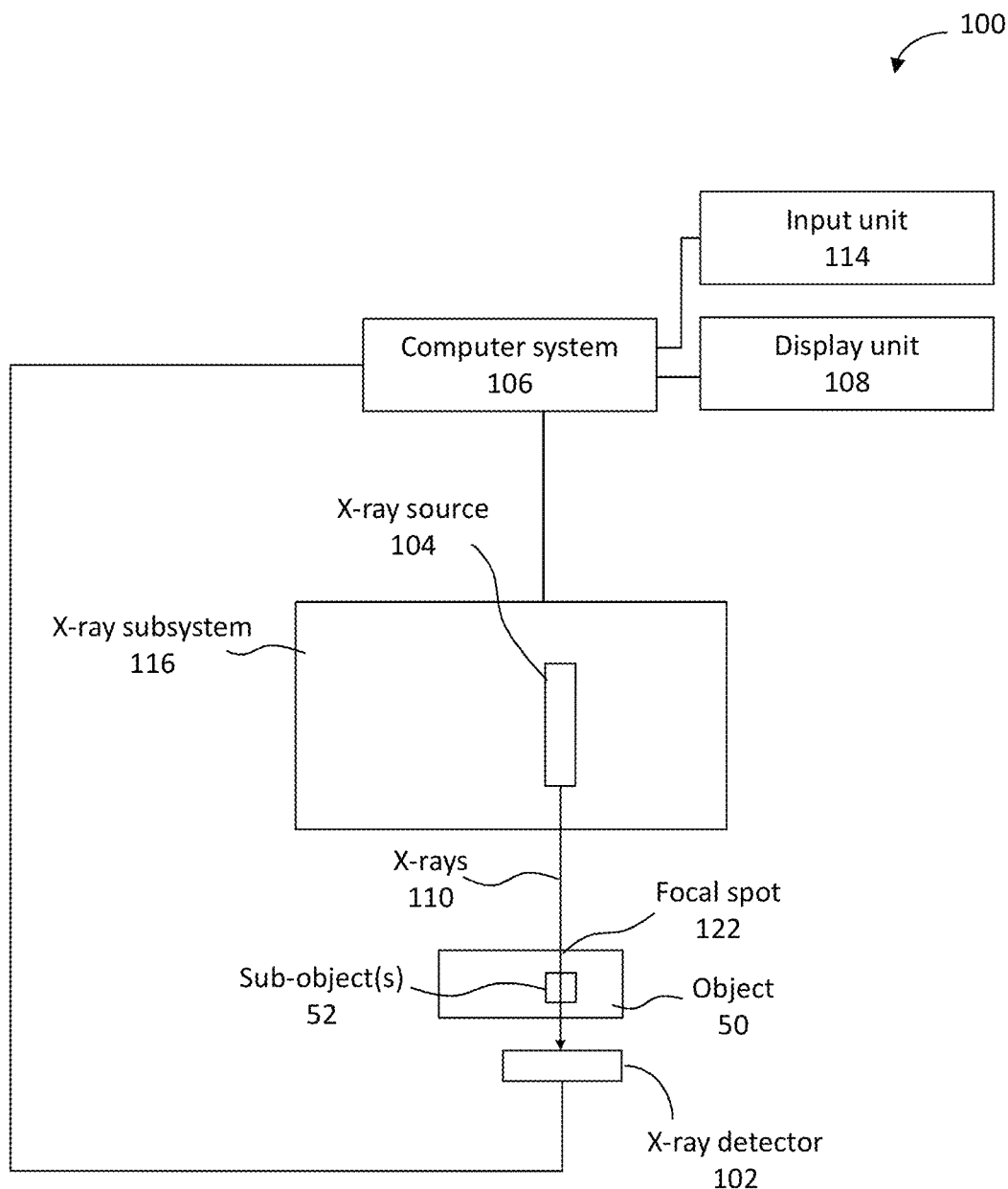
FIG. 1 is a block diagram of an x-ray imaging system.

Different ones of the figures may have at least some reference numerals that are the same in order to identify the same components, although a detailed description of each such component may not be provided below with respect to each figure.

DETAILED DESCRIPTION OF THE PREFERRED EMBODIMENTS

In accordance with example aspects described herein, systems and apparatuses are provided for intraoral x-ray image generation and x-ray collimation.

Figure 2:
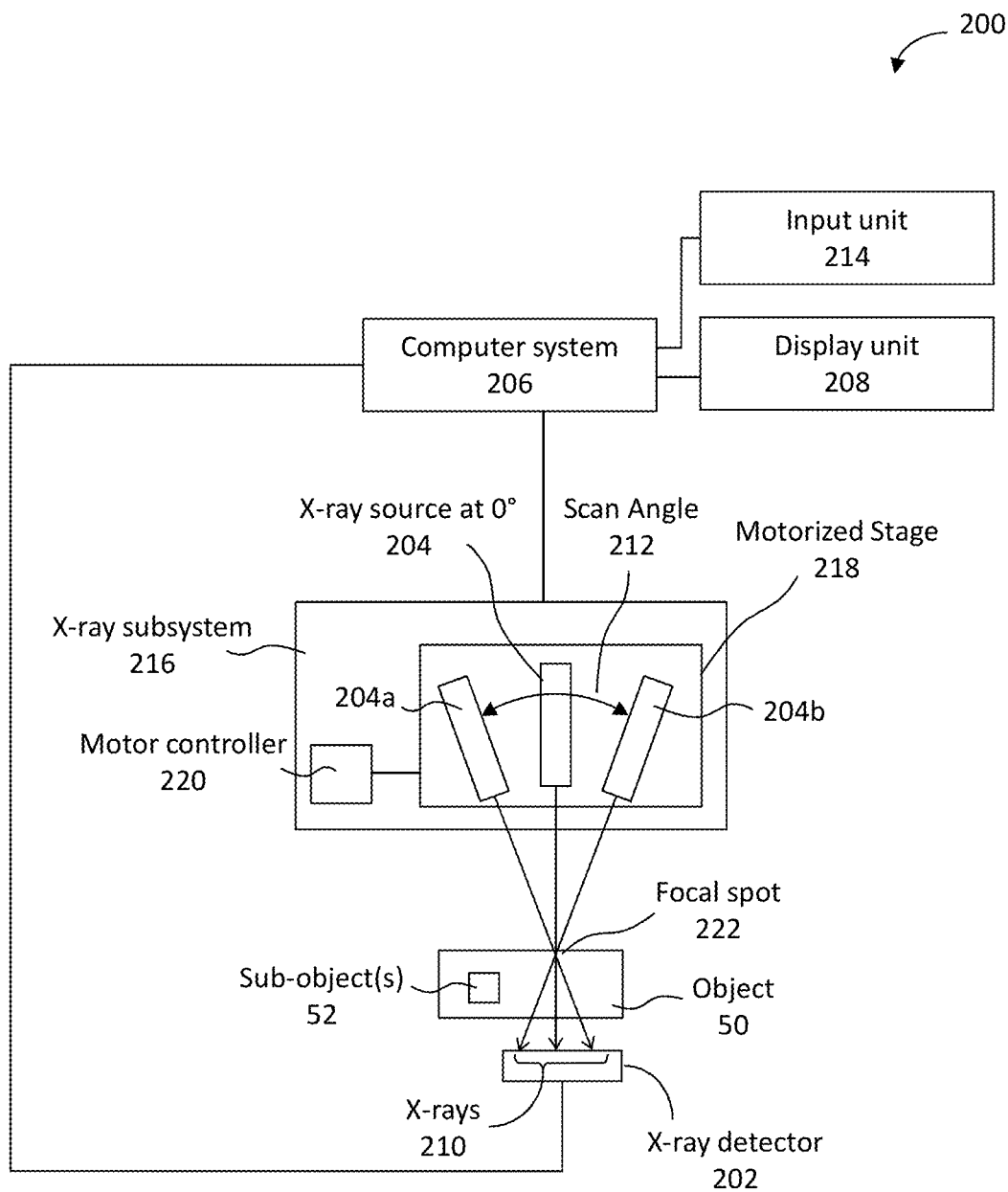
FIG. 2 is a block diagram of an intraoral tomosynthesis system.

The collimation device described herein can be used in any radiographic imaging system, including an x-ray imaging system 100 (shown in FIG. 1) and a tomosynthesis imaging system 200 (shown in FIG. 2). Those systems will now be described in further detail.

FIG. 1 is a block diagram of an x-ray imaging system 100. An x-ray source 104 emits x-rays 110 towards an object 50 that includes one or more sub-objects 52. The x-rays 110 penetrate object 50, but are attenuated as they travel through object 50. A sub-object 52 whose x-ray attenuation properties are different from the surrounding material will attenuate x-rays 110 differently from the surrounding material. Thus, if sub-object 52 has greater x-ray attenuation properties than the surrounding material, an x-ray beam that travels through sub-object 52 will be attenuated to a greater degree than a parallel x-ray that does not pass through sub-object 52. As a result, a portion of x-ray detector 102 that receives x-rays 110 that have passed through sub-object 52 will register a different energy value as compared to the parallel x-ray that did not pass through sub-object 52. These recorded energies (data) are transferred to a computer system 106 which forms a two-dimensional x-ray image that may be displayed on a display unit 108. The computer system 106 is communicatively connected to x-ray subsystem 116 and an input unit 114. The computer system 106 processes commands received through input unit 114 and configures the x-ray subsystem 116 accordingly.

FIG. 2 is a block diagram of an intraoral tomosynthesis system 200. Tomosynthesis provides three-dimensional information about a patient in the form of tomographic image slices reconstructed from images taken of the patient with an x-ray source from multiple perspectives within a scan angle smaller than that of computed tomography (CT) or cone-beam computed tomography (CBCT) (e.g., ±20°, compared with at least 180° in CBCT). In general, tomosynthesis can account for the depth of a sub-object in a way that a single two-dimensional x-ray cannot. The x-ray source translates about a center position while simultaneously rotating such that a centroid of the x-ray beam remains incident on the same focal spot. By this translation and rotation, the x-ray beam passing through the sub-object is incident on a different portion of the x-ray detector at each imaging position. This allows the computer system to obtain information about the depth of the sub-object that cannot be obtained by a single two-dimensional x-ray image.

As shown in FIG. 2, the system 200 includes an x-ray detector 202 and an x-ray subsystem 216, both of which, including subcomponents thereof, are electrically coupled to a computer system 206. In one example, the x-ray subsystem 216 hangs from a ceiling or wall-mounted mechanical arm, so as to be freely positioned relative to an object 50. The x-ray subsystem 216 further includes an x-ray source 204 mounted on a motorized stage 218 and an on-board motor controller 220. The on-board motor controller 220 controls the motion of the motorized stage 218.

The computer system 206 is electrically coupled to a display unit 208 and an input unit 214. The display unit 208 can be an output and/or input user interface.

The x-ray detector 202 is positioned on one side of the object 50 and the receiving surface of the x-ray detector 202 extends in an x-y plane in a Cartesian coordinate system. The x-ray detector 202 can be a small intraoral x-ray sensor that includes, for example, a complementary metal-oxide semiconductor (CMOS) digital detector array of pixels, a charge-coupled device (CCD) digital detector array of pixels, or the like. In an example embodiment herein, the size of the x-ray detector 202 varies according to the type of patient to whom object 50 belongs, and more particularly, the x-ray detector 202 may be one of a standard size employed in the dental industry. Examples of the standard dental sizes include a "Size-2" detector, which is approximately 27×37 mm in size and is typically used on adult patients, a "Size-1" detector, which is approximately 21×31 mm in size and is typically used on patients that are smaller than Size-2 adult patients, and a "Size-0" detector, which is approximately 20×26 mm in size and is typically used on pediatric patients. In a further example embodiment herein, each pixel of the x-ray detector 202 has a pixel width of 15 μm, and correspondingly, the Size-2 detector has approximately 4 million pixels in a 1700×2400 pixel array, the Size-1 detector has approximately 2.7 million pixels in a 1300×2000 pixel array, and the Size-0 detector has approximately 1.9 million pixels in a 1200×1600 pixel array. The color resolution of the x-ray detector 202 may be, in one example embodiment herein, a 12-bit grayscale resolution, although this example is not limiting, and other example color resolutions may include an 8-bit grayscale resolution, a 14-bit grayscale resolution, and a 16-bit grayscale resolution.

The x-ray source 204 is positioned on an opposite side of the object 50 from the x-ray detector 202. The x-ray source 204 emits x-rays 210 which pass through object 50 and are detected by the x-ray detector 202. The x-ray source 204 is oriented so as to emit x-rays 210 towards the receiving surface of the x-ray detector 202 in at least a z-axis direction of the Cartesian coordinate system, where the z-axis is orthogonal to the x-y plane associated with the receiving surface of the x-ray detector 202.

The x-ray source 204 can also emit x-rays 210 while positioned at each of multiple different locations within a scan angle 212, where a 0° position in the scan angle 212 corresponds to the position for emitting x-rays 210 along the z-axis. In one example embodiment herein, the user initially positions the x-ray subsystem 216, and hence, also the x-ray source 204, to a predetermined starting position relative to the object 50. The x-ray source 204 may include alignment aids for ensuring a correct position and alignment (discussed in further detail below). The computer system 206 then controls the on-board motor controller 220 to move the x-ray source 204 via the motorized stage 218, based on the known starting position, to step through each of the different locations within the scan angle 212. The computer system 206 controls the x-ray source 204 to cause the source 204 to emit x-rays 210 at each of those locations.

The centroid of the x-rays 210 passes through a focal spot 222 at each of the different locations within the scan angle 212. The focal spot 222 may be, for example, located close to the detector 202 such that x-rays 210 emitted from the x-ray source 204 positioned at the outer limits of the scan angle 212 are aimed at and do not miss the x-ray detector 202. In FIG. 2, the 0° position is represented by the x-ray source 204, while reference numerals 204a and 204b represent the same x-ray source 204 but in two other example positions within the scan angle 212. The scan angle 212 can be, for example, ±20° from the 0° position, although this example is not limiting.

Additionally, the motion of x-ray source 204 along the scan angle 212 may form different scan paths, such as, for example, a linear scan, a curved scan, or a circular scan. In the linear scan, the x-ray source 204 moves linearly in an x-y plane while emitting x-rays 210 toward the focal spot 222, forming a triangular sweep. In the curved scan, the x-ray source 204 moves in an arc while emitting x-rays 210 toward the focal spot 222, forming a fan beam sweep. In the circular scan, the x-ray source 204 rotates around the z-axis while emitting x-rays 210 toward the focal spot 222, forming a conical beam sweep. The scan positions may also be arranged in any particular one or more planes of the Cartesian coordinate system.

As emitted x-rays 210 pass through the object 50, photons of x-rays 210 will be more highly attenuated by high density structures of the object 50, such as calcium-rich teeth and bone, and less attenuated by soft tissues, such as gum and cheek. One or more of the attenuating structures can be sub-object(s) 52. X-rays 210 passing through and attenuated by object 50, are projected onto x-ray detector 202, which converts the x-rays 210 into electrical signals and provides the electrical signals to computer system 206. In one example embodiment, the x-ray detector 202 may be an indirect type of detector (e.g., a scintillator x-ray detector) that first converts x-rays 210 into an optical image and then converts the optical image into the electrical signals, and in another example embodiment, the x-ray detector 202 may be a direct type of detector (e.g., a semiconductor x-ray detector) that converts x-rays 210 directly into the electrical signals. The computer system 206 processes the electrical signals to form a two-dimensional projection image of the object 50. In one example embodiment herein, the image size of the two-dimensional projection image corresponds to the dimensions and the number of pixels of the x-ray detector 202.

The system 200 can collect a plurality of projection images, as described above, by first positioning the x-ray source 204 at different angles, including at least the 0° position, and emitting x-rays 210 at each of those different angles through object 50 towards x-ray detector 202. For example, the plurality of projection images may include a total of fifty-one projections: one orthogonal projection image, obtained when the x-ray source is at the 0° position, and fifty projection images, each obtained when the x-ray source 204 is positioned at different angles within a range of ±20° from the z-axis (corresponding to the scan angle 112). In other example embodiments, the number of projection images may range from twenty-five to seventy. Because the orthogonal projection image is obtained when the x-ray source is at the 0° position, the orthogonal projection image has the same appearance as an x-ray image. That is, the two-dimensional orthogonal projection image has no depth perception, and one or more sub-object(s) 52 within object 50 may appear overlaid one on top of another in the orthogonal projection image. On the other hand, sub-object(s) 52 at different depths of the z-axis within object 50 undergo varying degrees of parallax when imaged from different angles along the scan angle 112.

The computer system 206 processes the plurality of projection images to reconstruct a series of two-dimensional tomosynthesis image slices, also known as a tomosynthesis stack of images. Each image slice is parallel to the plane in which the receiving surface of the x-ray detector 202 extends and at different depths of the z-axis.

The computer system 206 further processes the tomosynthesis image slices in a manner to be described below, to generate clinically relevant information related to object 50 (e.g., a patient's dental anatomy), and in a further example embodiment herein, related to sub-object(s) 52. In one example embodiment herein, the computer system 206 obtains input from a user via input unit 214 and/or display unit 208 to guide the further processing of the tomosynthesis slices.

The orthogonal projection image, one or more image slices of the tomosynthesis stack, and the extracted information are provided by the computer system 206 for display to the user on the display unit 208.

Figure 3:
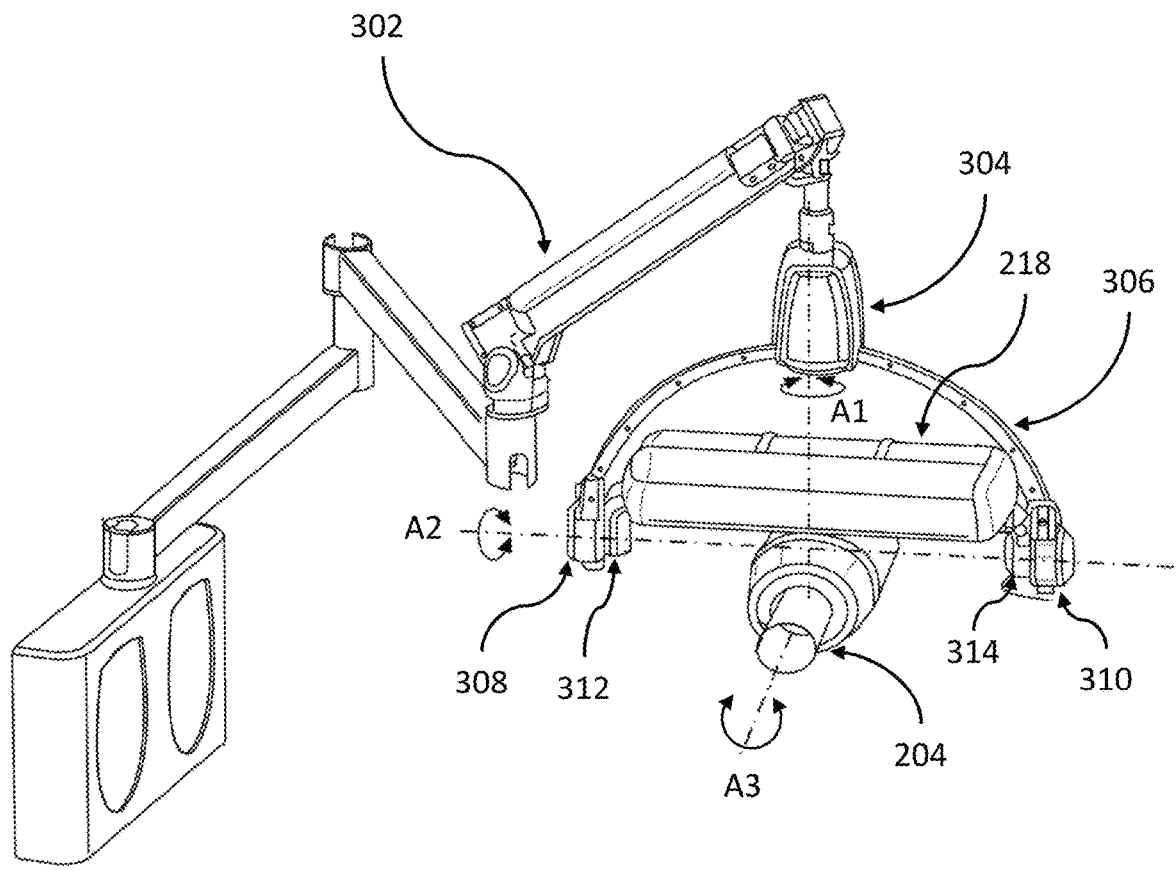
FIG. 3 is one embodiment an x-ray imaging system.

As shown in FIG. 3, the x-ray source 204 may be connected to an adjustable arm 302, which may be segmented and include one or more joints such as: a hinge, a swivel, a universal joint, or the like. The adjustable arm 302 allows the x-ray source 204 to freely translate in three-dimensional space. The x-ray source 204 may be connected to a collimation device 500. Attached to one end of the adjustable arm 302 is a vertical member 304. The other end of the adjustable arm 302 may be mounted to a stationary structure, such as a wall or a ceiling. The vertical member 304 is suspended vertically from the adjustable arm by a joint that allows the vertical member 304 to freely rotate about an axis (A1) substantially defined by the vertical member 304, regardless of the position and orientation of the adjustable arm 302. The vertical member 304 includes a bearing assembly which acts as a channel through the vertical member 304. A yoke 306 is movably constrained within the channel, and can be angularly displaced through the bearing assembly and thus through the vertical member 304, allowing rotation relative to axis A3. A brake may hold the yoke in place and substantially prevent any motion of the yoke 306 through the bearing assembly, thus locking the position of the yoke 306 relative to the vertical member 304. One or more brake release buttons may also be provided such that an operator can release the brake and allow the yoke 306 to rotate through the vertical member 304.

The motorized stage 218 may include arms 312 and 314 which are movably attached to the yoke ends 308 and 310, respectively, each point of attachment forming a pivot such that the motorized stage 118 can be pitched about an axis (A2) which is substantially defined by the yoke ends 308 and 310 and substantially orthogonal to the axis (A3) of the x-ray source 204. In the exemplary arrangement illustrated in FIG. 3, the x-ray source 204 may be appropriately positioned at any desired location in three-dimensional space such that the axis A3 of the x-ray source 204 is substantially perpendicular to the surface of the x-ray detector 202.

Figure 4A:
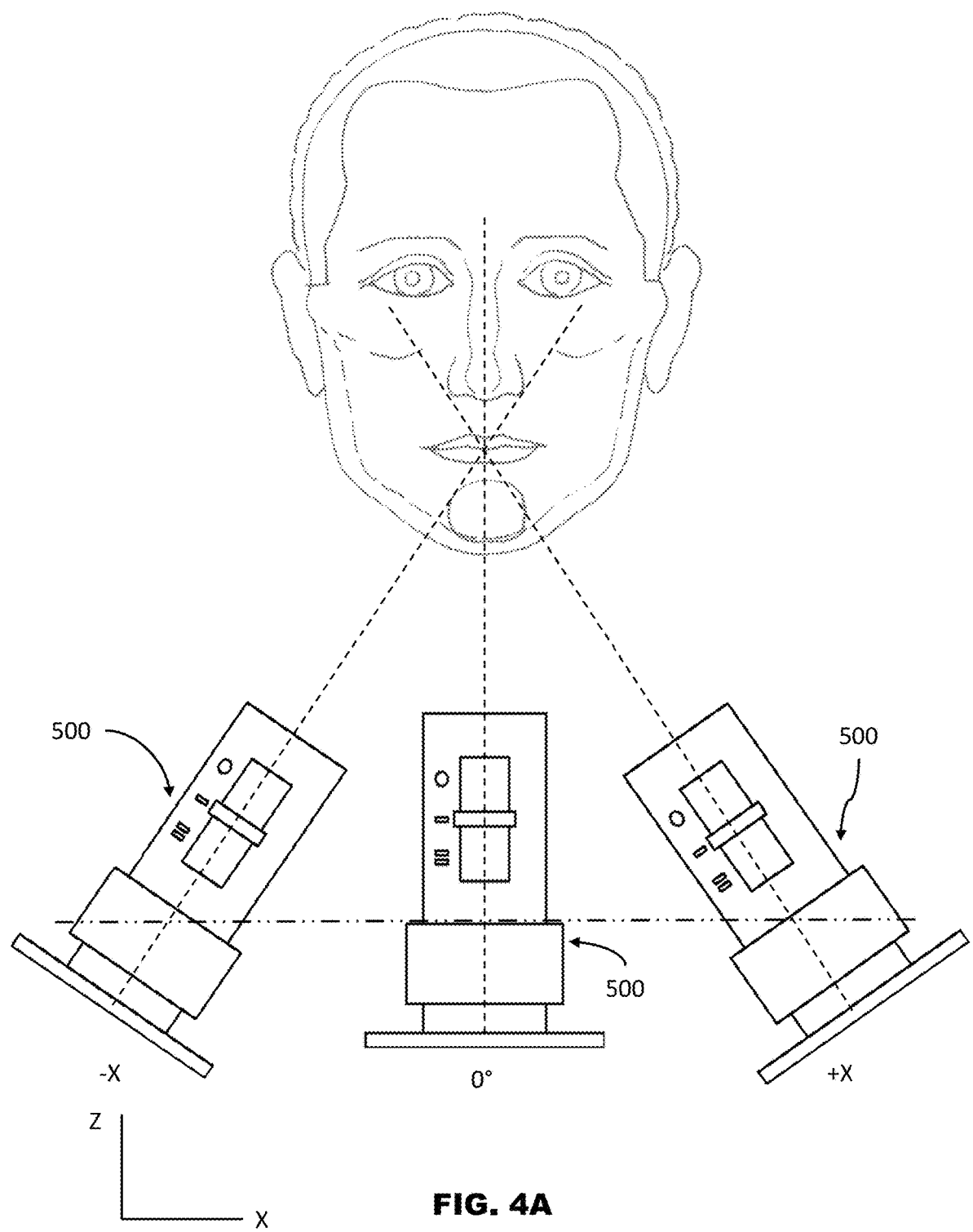
FIGS. 4A-C show a tomosynthesis imaging operation where the x-ray source is positioned below the patient's jaw.
Figure 4B:
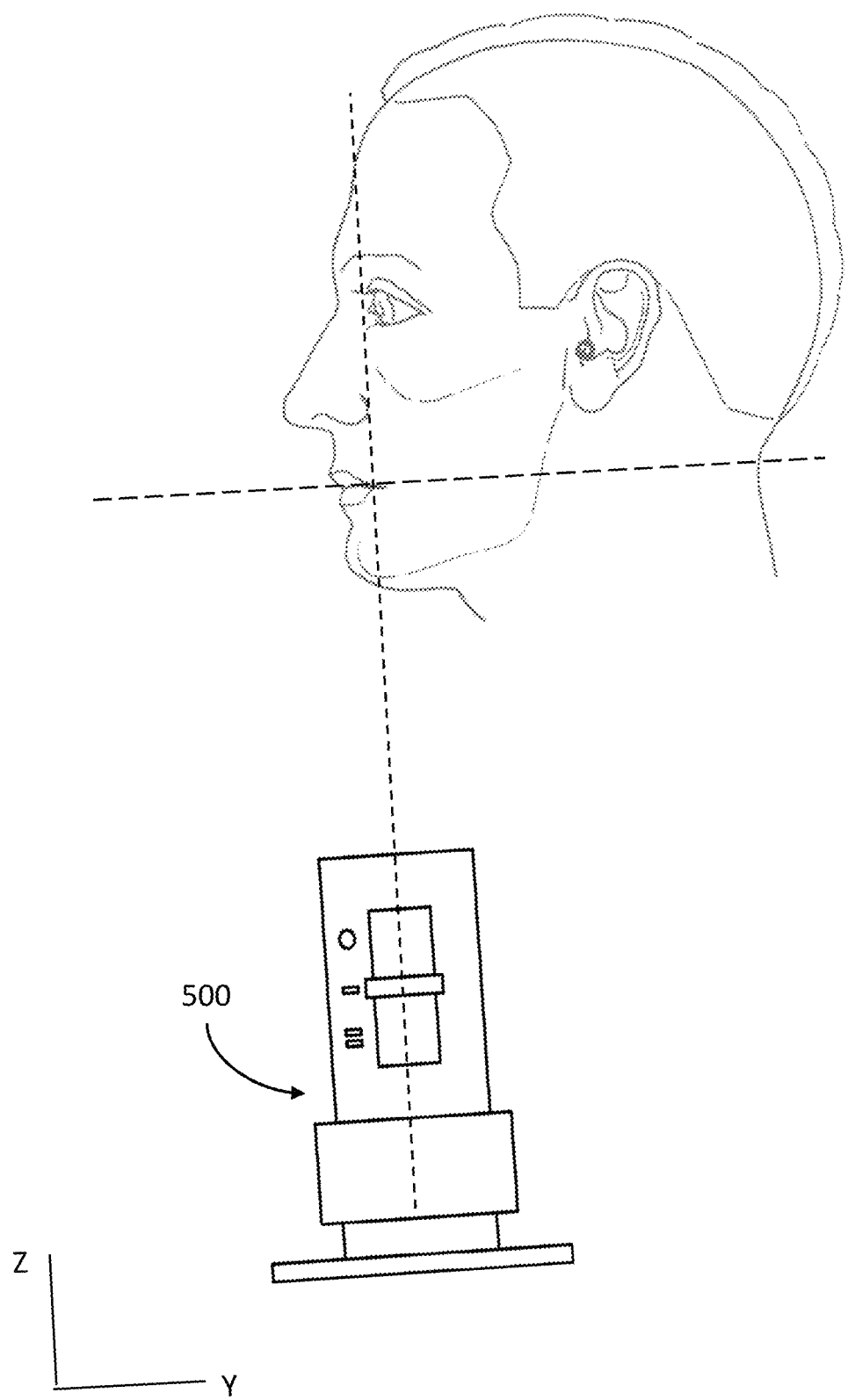
Figure 4C:
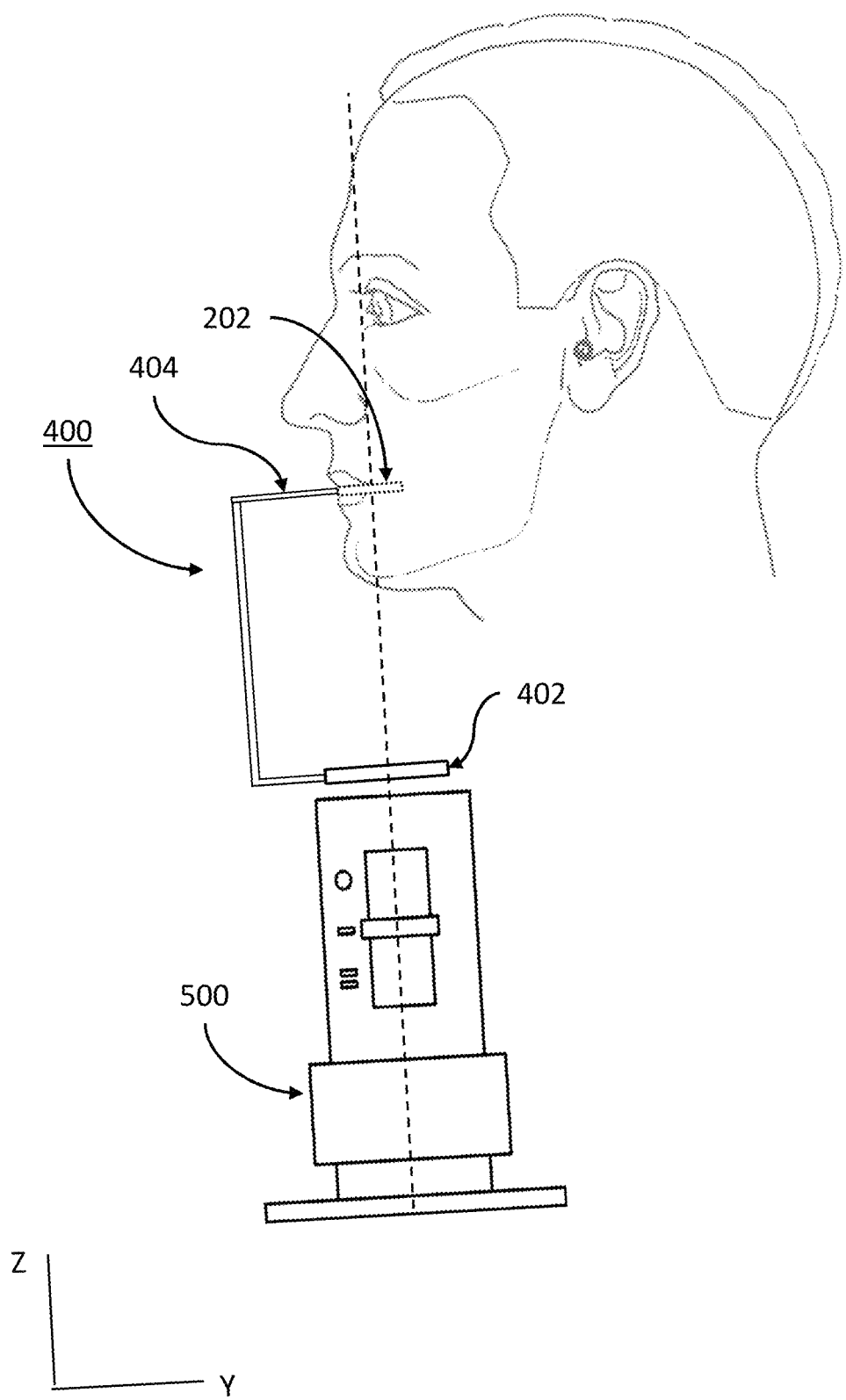

FIGS. 4A-C shows a tomosynthesis imaging operation where the x-ray source is positioned below the patient's jaw. For brevity, the collimation device 500 (which is connected to the x-ray source 204) is shown, rather than the entire x-ray source 204 and collimation device 500. The positioning of the x-ray source 204 below the patient's jaw is exemplary; the x-ray source 204 could be placed in any other position corresponding to a desired diagnostic view. In FIGS. 4A-C, the patient's teeth correspond to object 50 and sub-object(s) 52 illustrated in FIG. 1. For a tomosynthesis operation, the x-ray source 204 is initially positioned at the 0° position in the scan angle, which typically corresponds to a middle position in the scanning range. However, the x-ray source 204 may be initially positioned at any location within the scanning range. A single two-dimensional x-ray image generated at any one of the imaging positions within the scan range is equivalent to the result of an x-ray imaging operation, where the x-ray source 204 does not translate and rotate.

As shown in FIG. 4B, it is preferable that a plane corresponding to the surface of the x-ray detector 202 is orthogonal to the imaging direction of the x-ray source 204 in the y-z plane. As shown in FIG. 4C, an alignment device 400 may be provided to aid with the alignment of the x-ray source 204 relative to the x-ray detector 202. The alignment device 400 includes an alignment ring 402, also known as an aiming ring, disposed at one end of a connecting arm 404. The collimation device 500 may be placed in close proximity to the alignment ring, but with sufficient clearance that a user can see light being projected onto the ring. In one embodiment, where the alignment ring 402 and the collimation device 500 are the same diameter, the amount of clearance is approximately 2-3 cm of clearance. The other end of the connecting arm 404 is provided with a holder for holding the x-ray detector 202. In one embodiment, the connecting arm 404 may be integrated with the holder. The holder may be, for example, a plate with projections that retain the x-ray detector 202 against the plate. The holder may also use adhesive or a strap to secure the x-ray detector 202 to the plate.

Figure 5A:
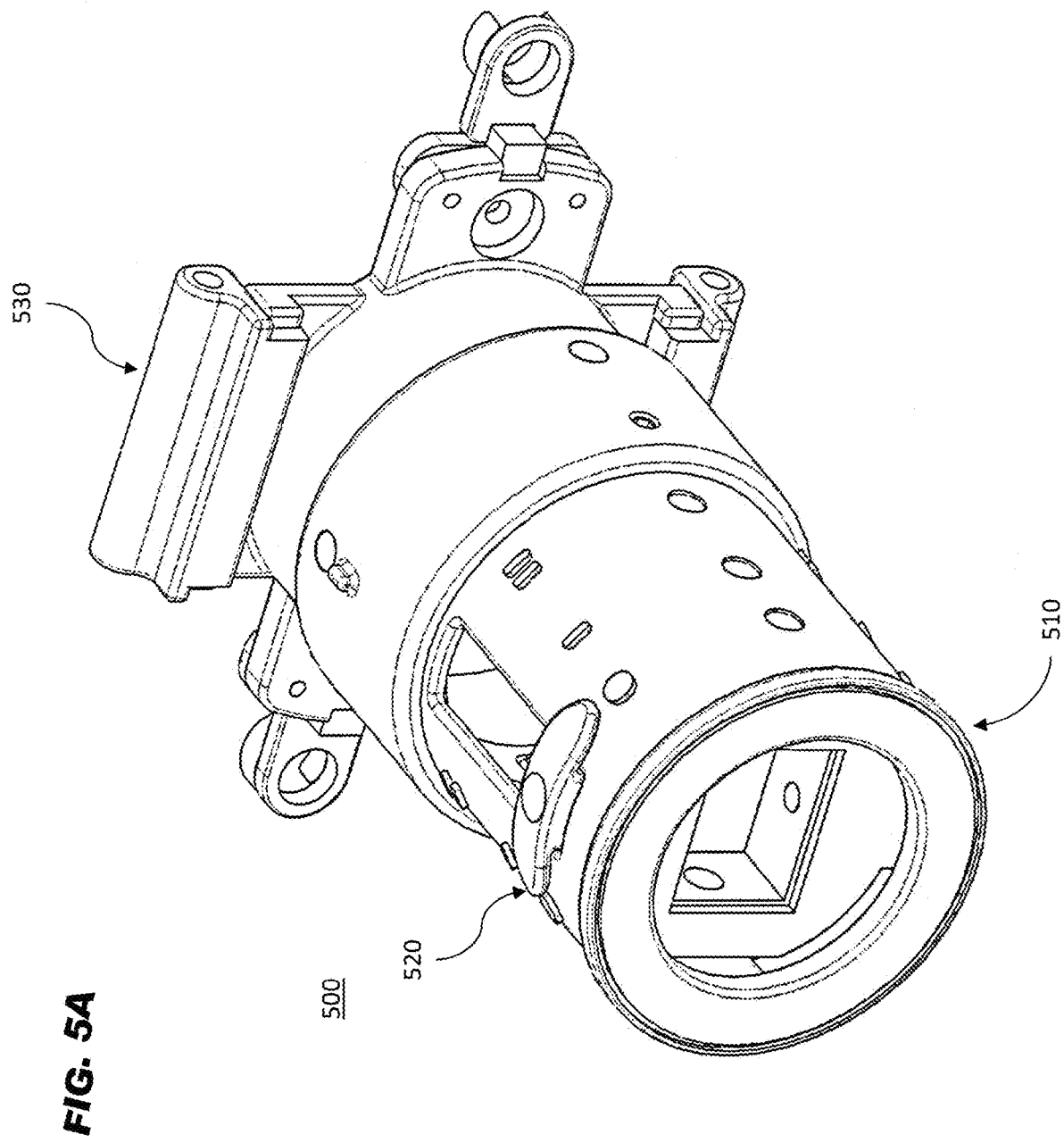
FIG. 5A is a perspective view of a collimation device according to one embodiment of the present invention in a horizontal position.
Figure 5C:
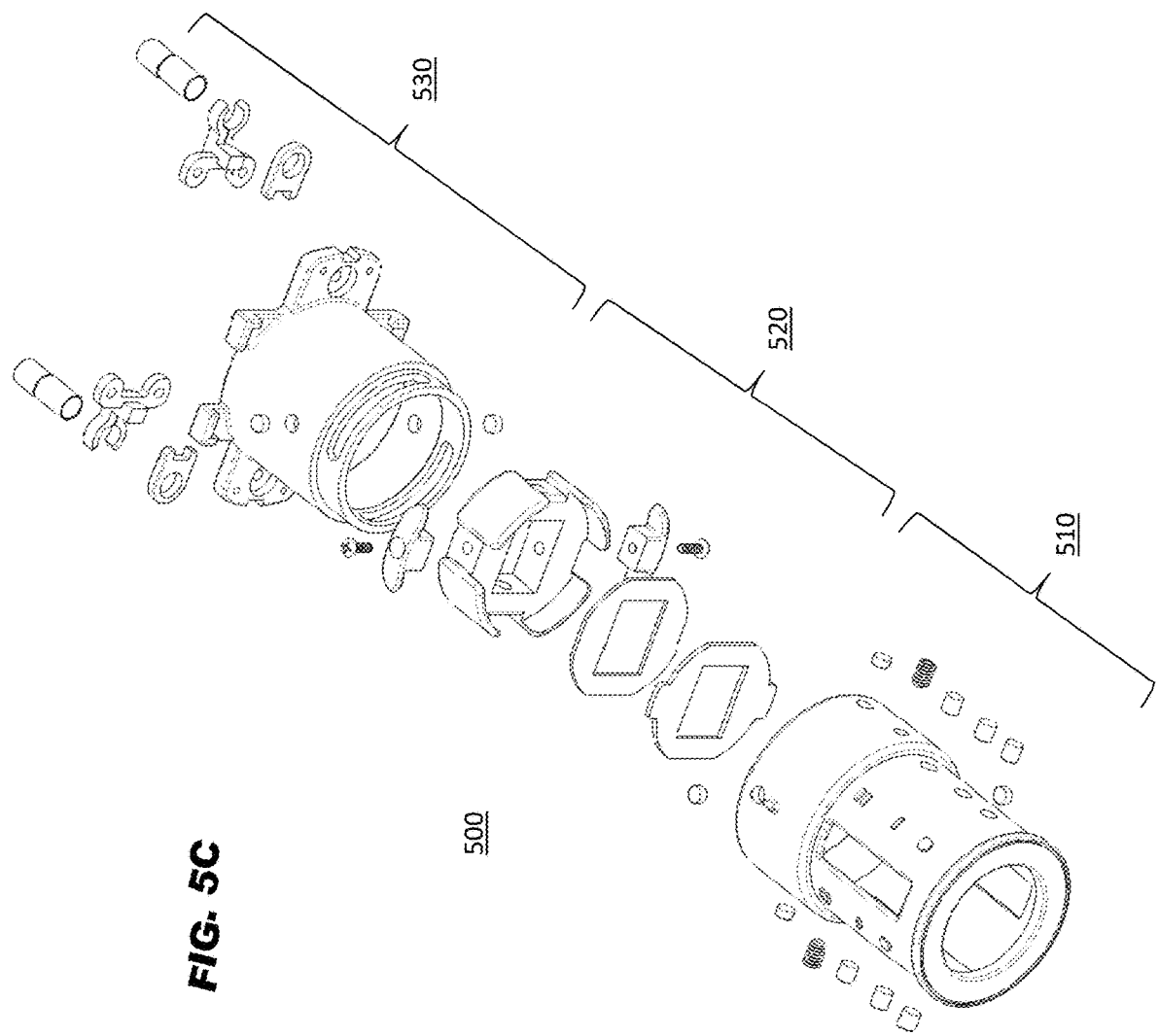
FIG. 5C is an exploded view of a collimation device according to one embodiment of the present invention.

To ensure that emitted x-rays are collimated to the imaging axis, each x-ray source 104/204 is connected to a collimation device 500 that is constructed to collimate the beam of x-rays. FIG. 5A is a perspective view of a collimation device 500 according to one embodiment of the present invention in a horizontal position (a first orientation), in which an aperture of the collimation device 500 is in a landscape orientation. FIG. 5B is a perspective view of the collimation device 500 according to one embodiment of the present invention in a vertical position (a second orientation), rotated 90° clockwise from the position shown in FIG. 5A, such that the aperture of the collimation device 500 is in a portrait orientation. FIG. 5C is an exploded view of collimation device 500. As illustrated in FIGS. 5A-C, the collimation device 500 may be divided into three main sections: collimator housing assembly 510, collimator mount assembly 520, and collimator chassis 530.

Figure 6A:
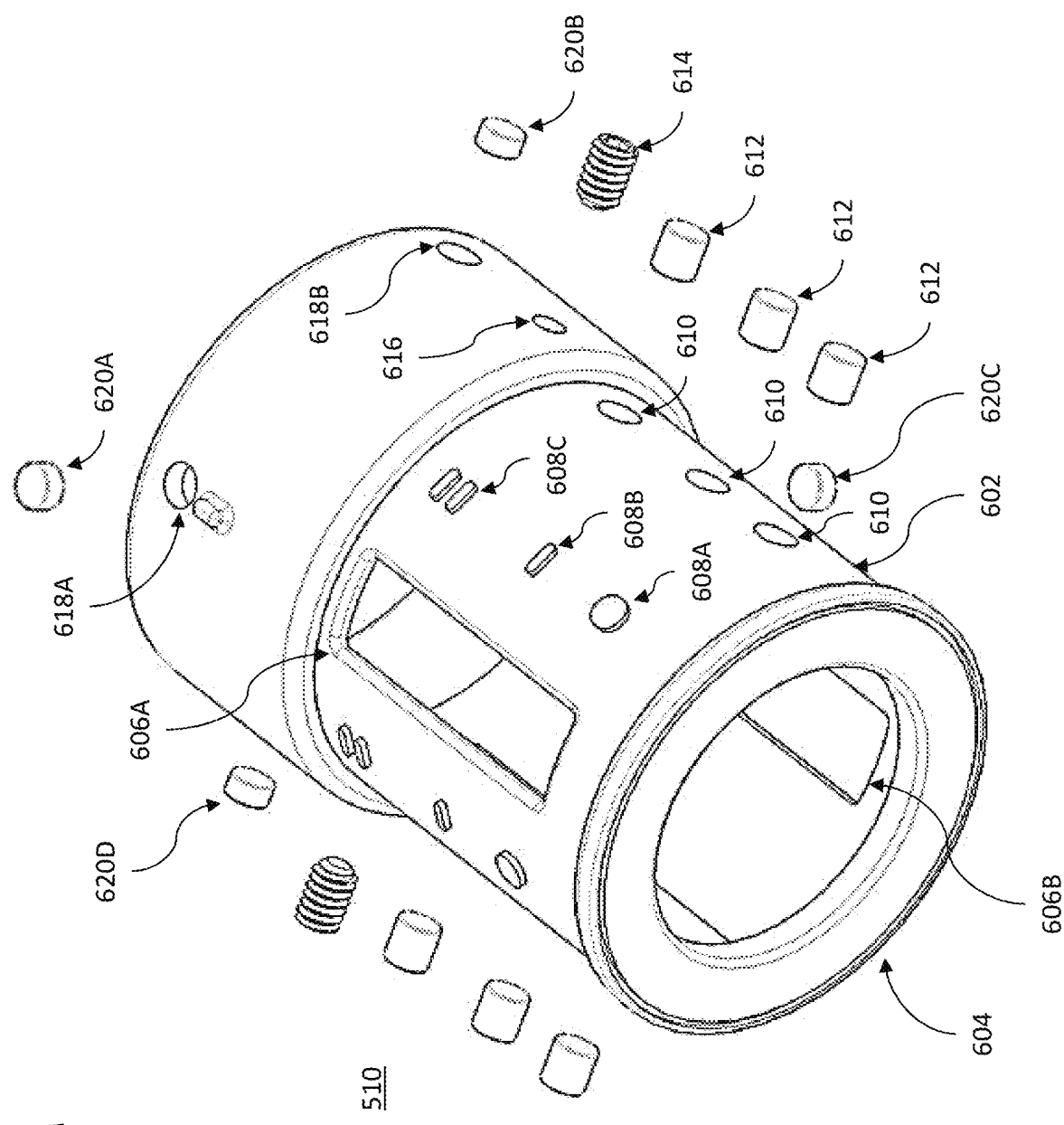
FIG. 6A is an exploded perspective view of a collimator housing assembly.

FIG. 6A is an exploded view of the collimator housing assembly 510. Collimator housing assembly 510 includes a collimator housing 602 that may be formed of plastic, metal, or other rigid or semi-rigid materials. The collimator housing 602 may include a light emitting alignment device 604 disposed proximate to or at one end thereof, in one embodiment. The light emitting alignment device may be aimed at a point on a longitudinal axis defined by the collimation device 500. The light emitting alignment device 604 may project optical light (i.e., wavelengths within the visible spectrum), laser light, or light that falls outside of the visible spectrum but which may be detected by an observation device such as a camera capable of detecting those wavelengths. As discussed below in greater detail, the light emitting alignment device 604 may be used to project a pattern onto the alignment ring 402 to aid in determining whether the collimation device 500 is correctly aligned and oriented relative to the intraoral imaging sensor (x-ray detector 202). While the light emitting alignment device 604 shown in FIG. 6A projects a circular pattern, the disclosure is not limited thereto. The light emitting alignment device 604 may project patterns of other shapes including, for example, a square pattern, a triangular pattern, or a regular polygon with n number of sides, where n is greater than or equal to 5. In another embodiment, the light emitting alignment device 604 may emit a pair of parallel lines, cross-line laser marks, or four dots that define a rectangle. The emitted pattern preferably corresponds to a pattern on the alignment ring 402 (as discussed below). For example, if the alignment ring 402 includes four depressions defining corners of a rectangle, the emitted pattern should be four dots. The light emitting alignment device 604 may also be located at a different location. For example, the light emitting alignment device 604 could be mounted on the collimator chassis 530 or one of the x-ray system components shown in FIG. 3, such as: the x-ray source 204, the motorized stage 218, yoke ends 308 and 310, or arms 312 and 314.

The collimator housing 602 includes a plurality of collimator mount positioning slots 606A and 606B disposed, in an exemplary embodiment, 180° degrees apart, i.e. on opposite sides of the collimator housing 602. In one embodiment, slots 606A and 606B are rectangular in shape. Of course, slots 606A and 606B may be of a different shape. Moreover, more than two slots may be provided, or only a single slot may be provided. Slots 606A and 606B allow for respective portions of the collimator mount assembly 520 to project beyond the collimator housing 602. An operator may manipulate the portions of the collimator mount assembly 520 and apply a force that causes the collimator mount assembly 520 to move relative to the collimator housing 602. Collimator mount assembly 520 is therefore moveable within the slots 606A and 606B to different positions in the longitudinal direction of the collimation device 500. On each side of slot 606A are position indicators 608A, 608B, and 608C corresponding to different sized intraoral sensors. Position indicator 608A indicates a desired position of the collimator mount assembly 520 for a Size-0 intraoral sensor. Position indicator 608B indicates a desired position of the collimator mount assembly 520 for a Size-1 intraoral sensor. Position indicator 608C indicates a desired position of the collimator mount assembly 520 for a Size-2 intraoral sensor. While the position indicators 608A, 608B, and 608C are shown on both sides of slot 606A, this is just exemplary. The position indicators could also be located on one side of slot 606A. The positioning indicators 608A, 608B, and 608C may be roman numerals, Arabic numerals, or any other letter or symbols.

The collimator housing 602 also includes a plurality of positioning holes 610. Each of the positioning holes 610 is sized to receive a collimator housing positioning magnet 612. The collimator positioning magnets 612 act in conjunction with collimator mount positioning magnets 632A and 632B to index the collimator mount 510 at the desired position (for a chosen sensor size). The indexing may be achieved also by use of detents, spring pins and holes and other methods. Thus, for example, if a Size-0 intraoral sensor is used, collimator positioning magnets 612 are inserted into position holes 610 located beneath position indicator 608A. The attraction between the collimator positioning magnets 612 and the collimator mount positioning magnets 632A and 632B resist any force acting on the collimator mount assembly 520 that may cause the collimator mount assembly 520 to move out of position.

As discussed below, the collimator housing 602 may rotate with respect to the collimator chassis 530. To facilitate this relative rotation while simultaneously ensuring that the collimator housing assembly 510 remains connected to the collimator chassis 530, lock screws 614 are provided through threaded holes 616 in the collimator housing 602 and engage, respectively, guide tracks 640A-B in the collimator chassis body 638. With this configuration, the collimator housing 602 may rotate with respect to the collimator chassis 530. In an exemplary embodiment, the collimator housing 602 can rotate clockwise 90° from a first orientation (shown in FIGS. 5A and 6A) to a second orientation (shown in FIG. 5B). Of course, this configuration is only exemplary. Collimation device 500 may be configured so that collimator housing 602 rotates counterclockwise relative to the collimator chassis 530 and through a different angle range, e.g., up to 180°.

To assist in aligning, the collimator housing 602 with the collimator chassis 530 at the different orientations, a plurality of indexing elements may be provided. For example, the plurality of indexing elements may include a plurality of magnets located in the collimator housing 602 and the collimator chassis body 638. More specifically, a plurality of magnets 620A-D may be placed in a plurality of magnet holes 618A-D, respectively. The plurality of magnets 620A-D may be grouped into two pairs, a first pair of magnets 620A and 620C and a second pair of magnets 620B and 620D. Each of these pairs may be considered a pair of indexing elements. Magnets 642A and 642B in the collimator chassis may also be considered a pair of indexing elements. In one embodiment, each of the magnets 620A-D are placed 90° apart from each. Thus, when the collimator housing 602 is in the first orientation (shown in FIG. 6A) magnets 620A and 620C (the first pair of magnets) are proximate to and attracted to corresponding magnets 642A and 642B (a third pair of magnets) in the collimator chassis 530. The attractive force between magnets 620A and 620C and the corresponding magnets 642A and 642B in the collimator chassis 530 create a resistance to rotational motion, such that undesired rotational forces that may act on the collimator housing assembly 510 do not cause an undesired rotation. Similarly, when the collimator housing 602 is in a second orientation (rotated by 90° from the first orientation), magnets 620B and 620D (the second pair of magnets) are proximate to and attracted to corresponding magnets 642A and 642B in the collimator chassis 530. The attractive force between magnets 620B and 620D and the corresponding magnets 642A and 642B in the collimator chassis 530 create a similar resistance to rotational motion such that undesired rotational forces that may act on the collimator housing assembly 510 do not cause an undesired rotation.

In one embodiment, other indexing element besides magnets may be provided to maintain a relative orientation between the collimator housing 602 and the collimator chassis 530. The indexing elements may include mechanical connections. For example, collimator chassis body 638 may be provided with spring loaded pins in place of the magnets 642A and 642B, and the collimator housing may be provided with detents in place of magnets 620A-D. The pins may be driven by springs into the detents and thus create a resistance to an undesired rotational force that may act on the collimator housing assembly 510. Of course, this resistance may be overcome by a sufficient force (e.g., by an operator) thus allowing the rotation of the collimator housing assembly 510 relative to the collimator chassis 530. In this case, detents located where magnets 620A and 620C are shown would be a first pair of indexing elements, detents located where magnets 620B and 620C are shown would be a second pair of indexing elements, and spring loaded pins located where magnets 642A and 642B are shown would be a third pair of indexing elements.

Figure 6B:
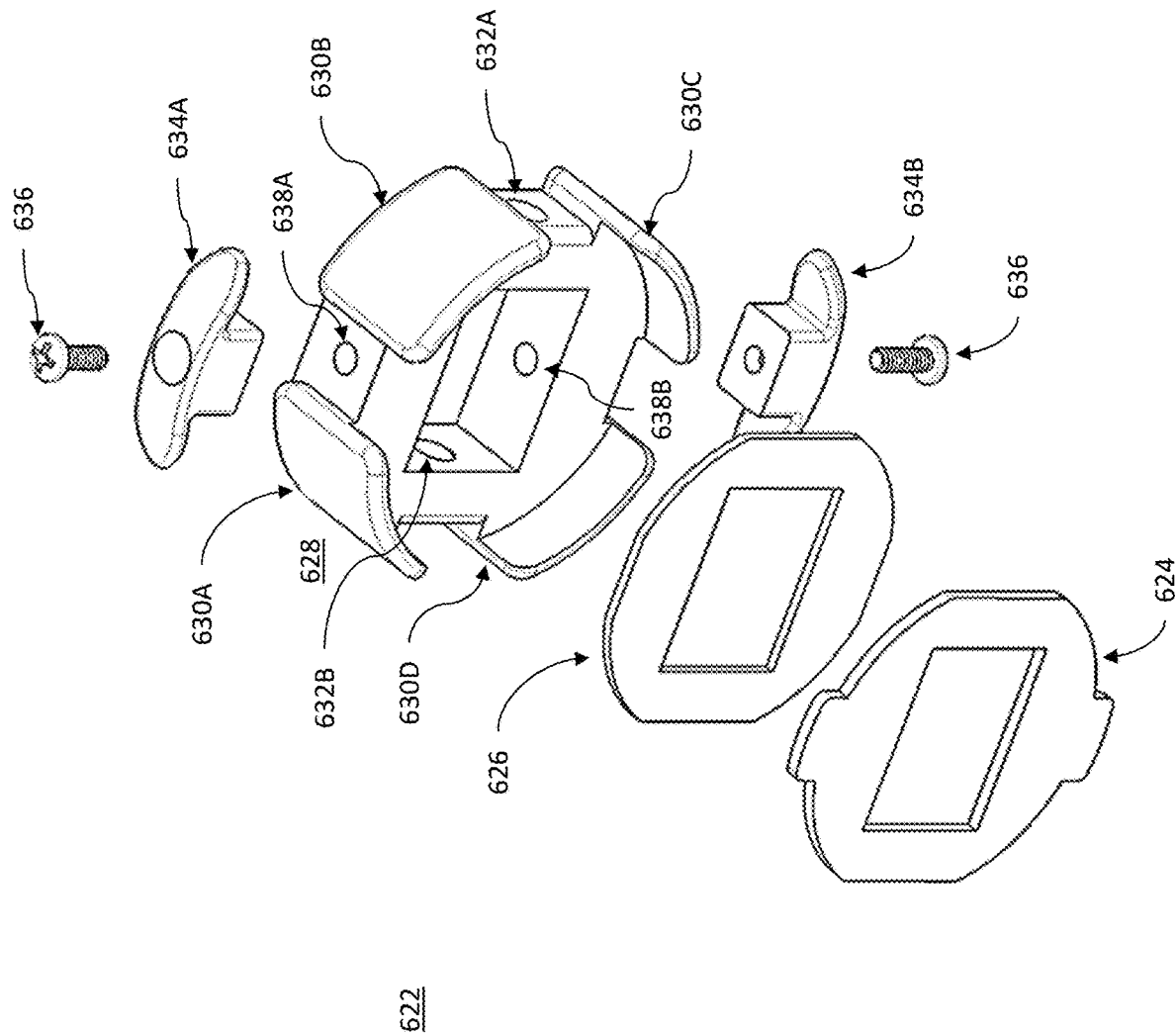
FIG. 6B is an exploded perspective view of the collimator mount assembly.

FIG. 6B is an exploded perspective view of the collimator mount assembly 520. The collimator mount assembly 520 includes a collimator cover 624 and a collimator plate 626. Thus, the collimator plate is movable with the collimator mount assembly 520. The collimator plate 626 is made of lead or another x-ray absorbing material and thus strongly attenuates x-rays incident thereon, blocking their passage (≥99% of the x-rays are blocked in one embodiment). The collimator plate 626 has a rectangular aperture that allows x-rays from the x-ray source 104/204 to pass. The size of the rectangular aperture in the collimator plate 626 is related to the different positions of the collimator mount assembly 520 and the anticipated distance between the x-ray source 204 and the x-ray detector 202, and may be calculated based on such information. In one embodiment, the distance between the x-ray source 204 and the x-ray detector 202 is 12.0 inches±0.5 inches. The rectangular aperture is sized so that at each position the corresponding sensor is fully illuminated but there is minimal overexposure, i.e. the cross-sectional area of the beam is equal to or slightly larger than the area of the sensor. For example, when the collimator mount assembly 520 is at the Size-0 position, a Size-0 sensor (with an approximate size of 20×26 mm) is fully illuminated with little overage. Moving the collimator mount assembly 520 to the Size-1 position, i.e. closer to the x-ray source 204, increases the size of the x-ray beam such that the Size-1 sensor (with an approximate size of 21×31 mm) is fully illuminated with little overage. Moving the collimator mount assembly to the Size-2 position, i.e. even closer to the x-ray source 204, further increases the size of the x-ray beam such that the Size-2 sensor (with an approximate size of 27×37 mm) is fully illuminated with little overage.

The collimator mount assembly 520 further includes a collimator mount body 628. The collimator mount body 628 includes four curved flanges 630A-D that are sized and shaped to engage an inner surface of the collimator housing 602. Flange 630B and 630C are spaced apart (in the vertical direction in FIG. 6B) by a distance equal to the size of first interior guide rail 652 located within the collimator housing 602. Similarly, flanges 630A and 630D are also spaced apart by a distance equal to the size of a second interior guide rail located within the collimator housing 602, 180° from the first interior guide rail 652. When collimation device 500 is assembled, the collimator mount assembly 520 is movable on the first interior guide rail and the second interior guide rail to the different positions. In an exemplary embodiment, the position holes 610 project through the interior guide rails and are coaxial with the collimator mount positioning magnets 632A and 632B in the collimator mount body 628. This allows for the positioning magnets 612 inserted into the position holes 610 to be in close proximity to the collimator mount positioning magnets 632A and 632B in the collimator mount body 628.

As discussed above, the collimator mount assembly 520 is able to move to a plurality of positions within the collimation device 500. To facilitate that movement, first and second handle pieces 634A and 634B are attached to the collimator mount body 628 using screws 636A which are inserted into threaded handle piece holes 636B. A portion of each of the first and second handle pieces 634A and 634B protrudes from slots 606A and 606B thus providing a grip for an operator to grab.

Figure 6C:
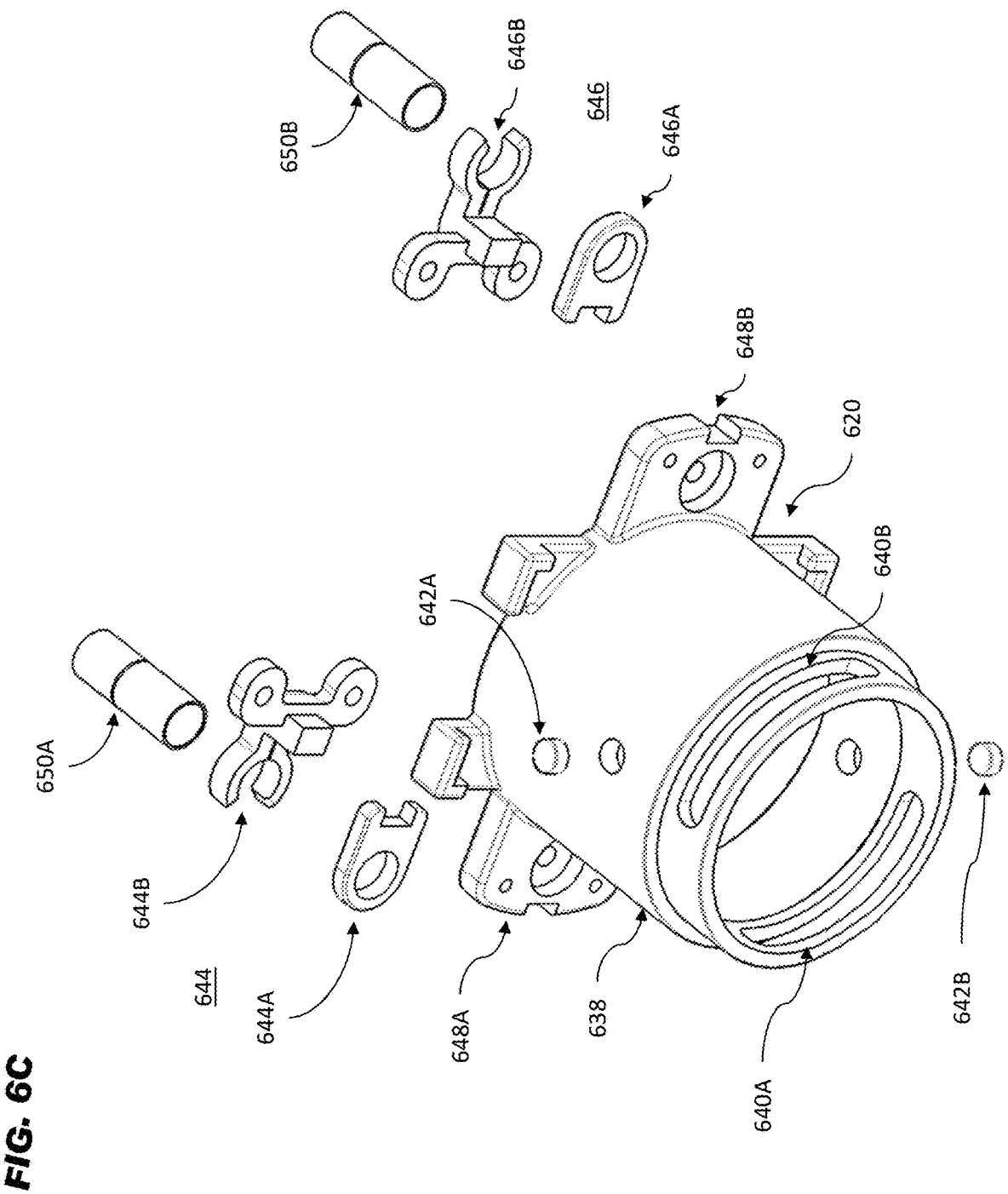
FIG. 6C is an exploded perspective view of a collimator chassis.

FIG. 6C is an exploded view of the collimator chassis 530. The collimator chassis 530 includes a collimator chassis body 638. The collimator chassis body 638 includes, near one end, a plurality of guide tracks 640A and 640B which, as discussed above, allow lock screws 614 to slide from one end to the other. This allows for the collimator housing 602 to be rotatable relative to the collimator chassis 530. The collimator chassis body 638 receives the x-ray beam from an x-ray source 104/204 at an opposite end from where the guide tracks 640A and 640B are located. The collimator chassis body 638 also includes recessed magnets 642A and 642B which are located on the top and bottom of the collimator chassis body 638, 180° degrees apart. Magnets 642A and 642B are attracted to magnets 620A-D (depending on the orientation) so that, as described above, when the collimator housing 602 is in the first and second orientations relative to the collimator chassis 530 there is a resistance to rotational forces that may cause undesired rotational motion of the collimator housing 602 relative to the collimator chassis 530.

In the embodiment shown in FIG. 6C, two laser mounting brackets 644 and 646 are attached to collimator chassis flange portions 648A and 648B. Laser mounting bracket 644 includes a first mounting piece 644A which includes a circular opening for receiving a laser 650A. Laser mounting bracket 644 also includes a second mounting piece 644B that includes a c-shaped aperture for receiving laser 650A.

When the first mounting piece 644A and the second mounting piece 644B are attached to the collimator chassis flange portion 648A they provide a structural support for the laser 650A. In a similar fashion, laser mounting bracket 646 includes a first mounting piece 646A which includes a circular opening for receiving a laser 650B. Laser mounting bracket 646 also includes a second mounting piece 646B that includes a c-shaped aperture for receiving laser 650B. When the first mounting piece 646A and the second mounting piece 646B are attached to the collimator chassis flange portion 648B they provide a structural support for the laser 650B.

Figure 7A:
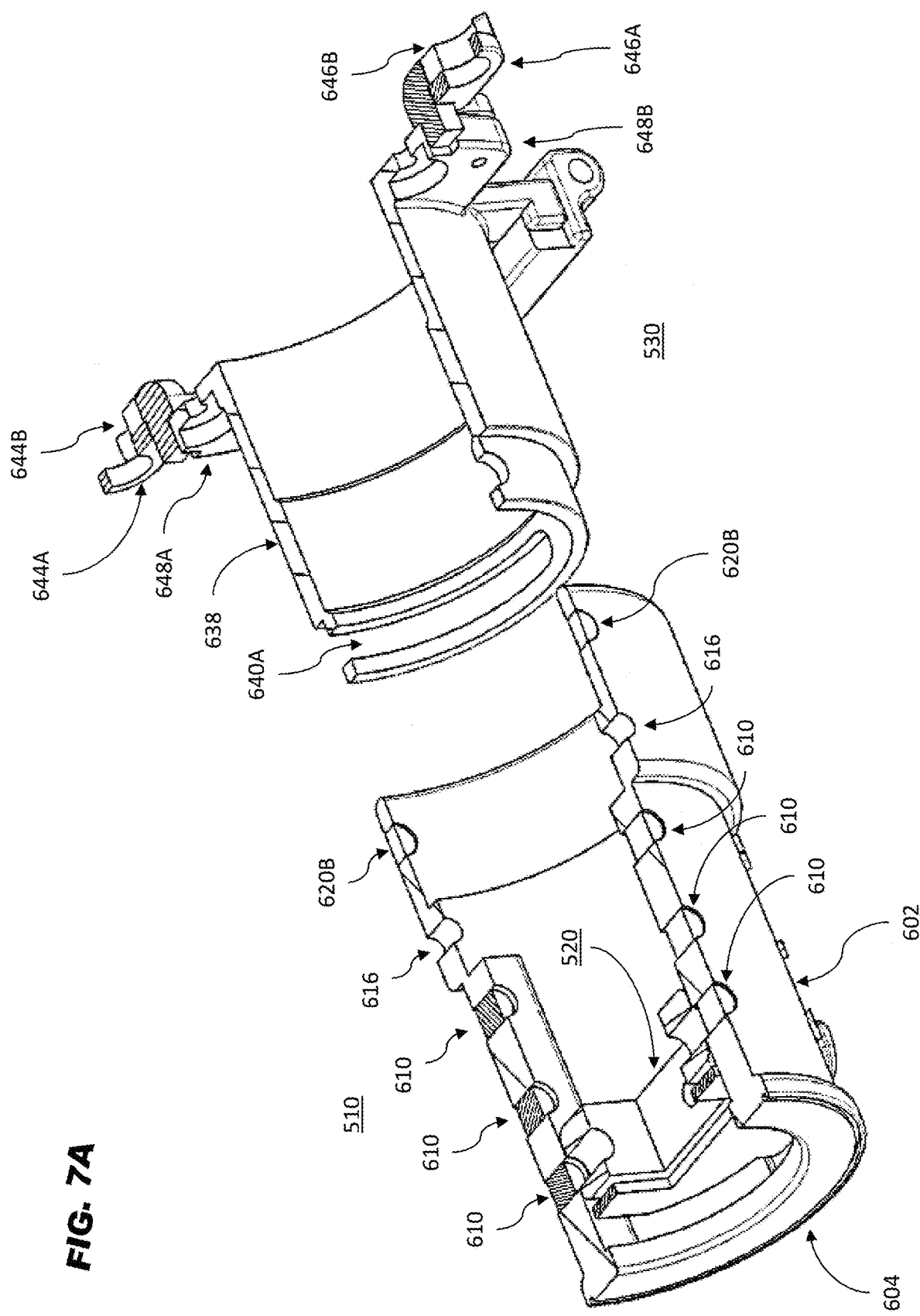
Figure 7C:
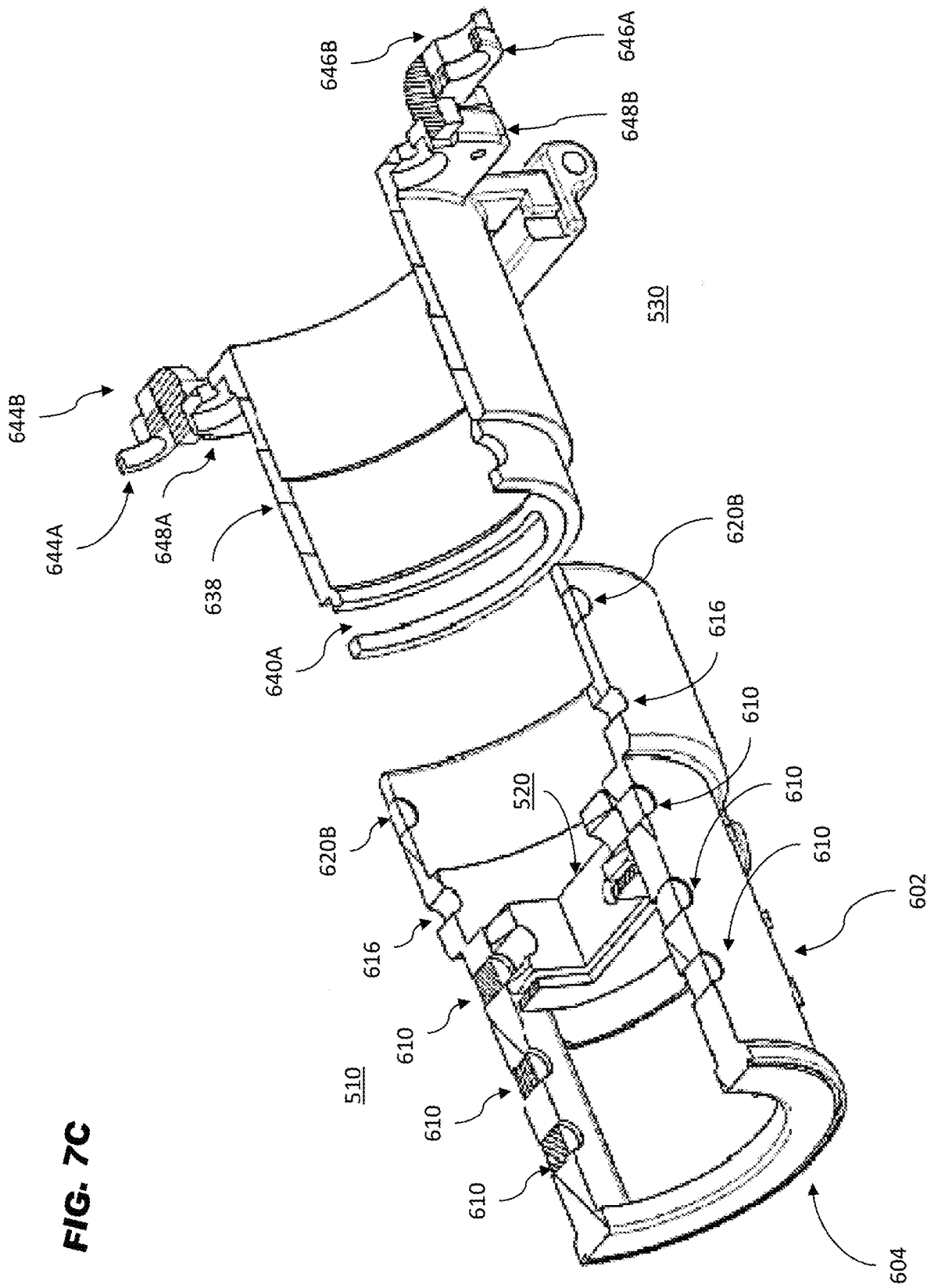

FIGS. 7A-C are sectional views of the collimation device 500 showing the collimator mount assembly 520 at three different positions, respectively corresponding to the Size-0, Size-1, and Size-2 intraoral sensors. In FIG. 7A, the collimator mount assembly 520 is at a position corresponding to Size-0 sensor. FIG. 7B shows the collimator mount assembly 520 at a position corresponding to a Size-1 sensor. FIG. 7C shows the collimator mount assembly 520 at a position corresponding to a Size-2 sensor. To secure the collimator mount assembly 520 at any one of these positions, positioning magnets 612 are inserted into the corresponding positioning holes 610 which are then attracted the collimator mount positioning magnets 632A and 632B.

Figure 8:
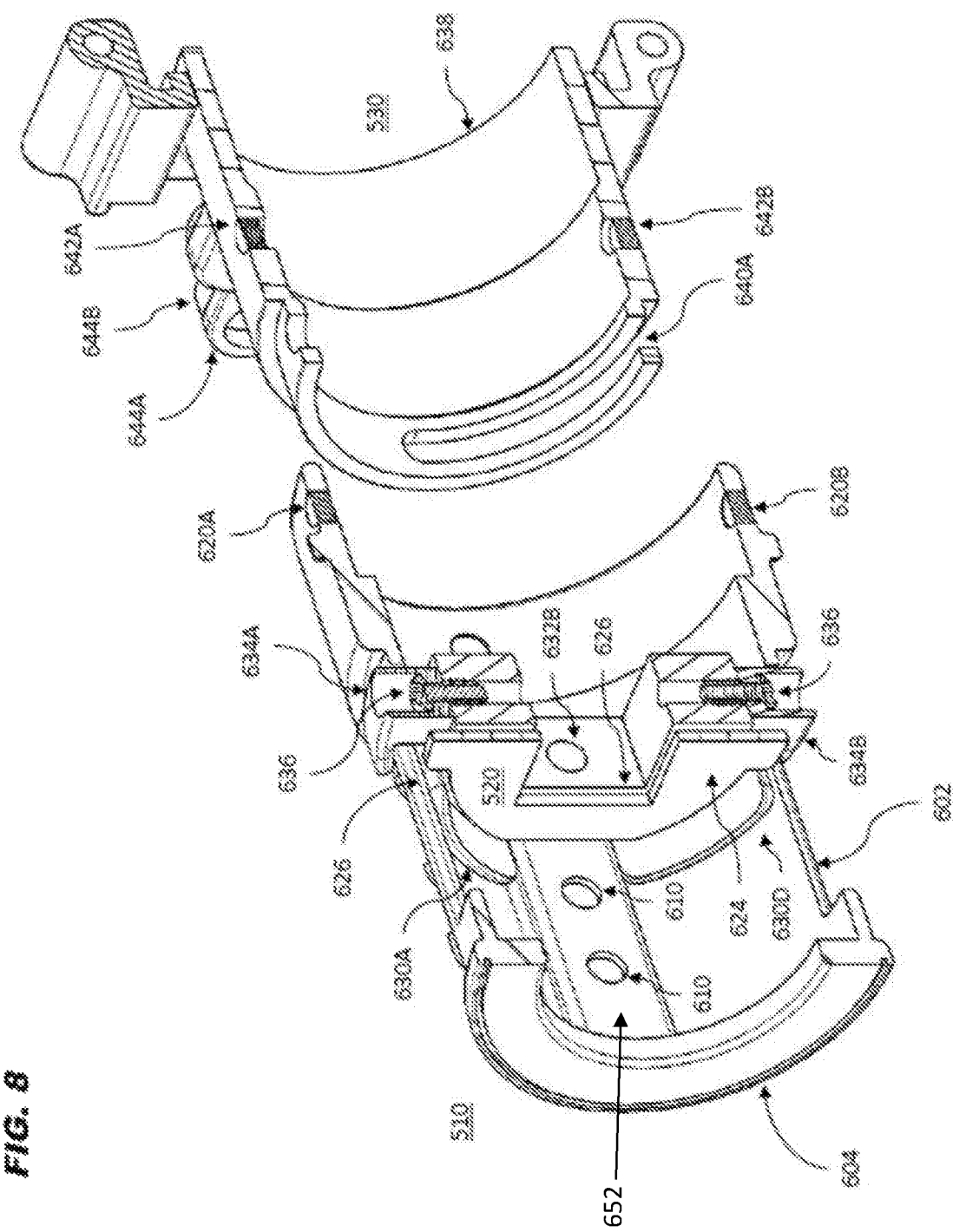
FIG. 8 is a sectional view rotated ninety degrees to the views in FIGS. 7A-C.
Figure 9:
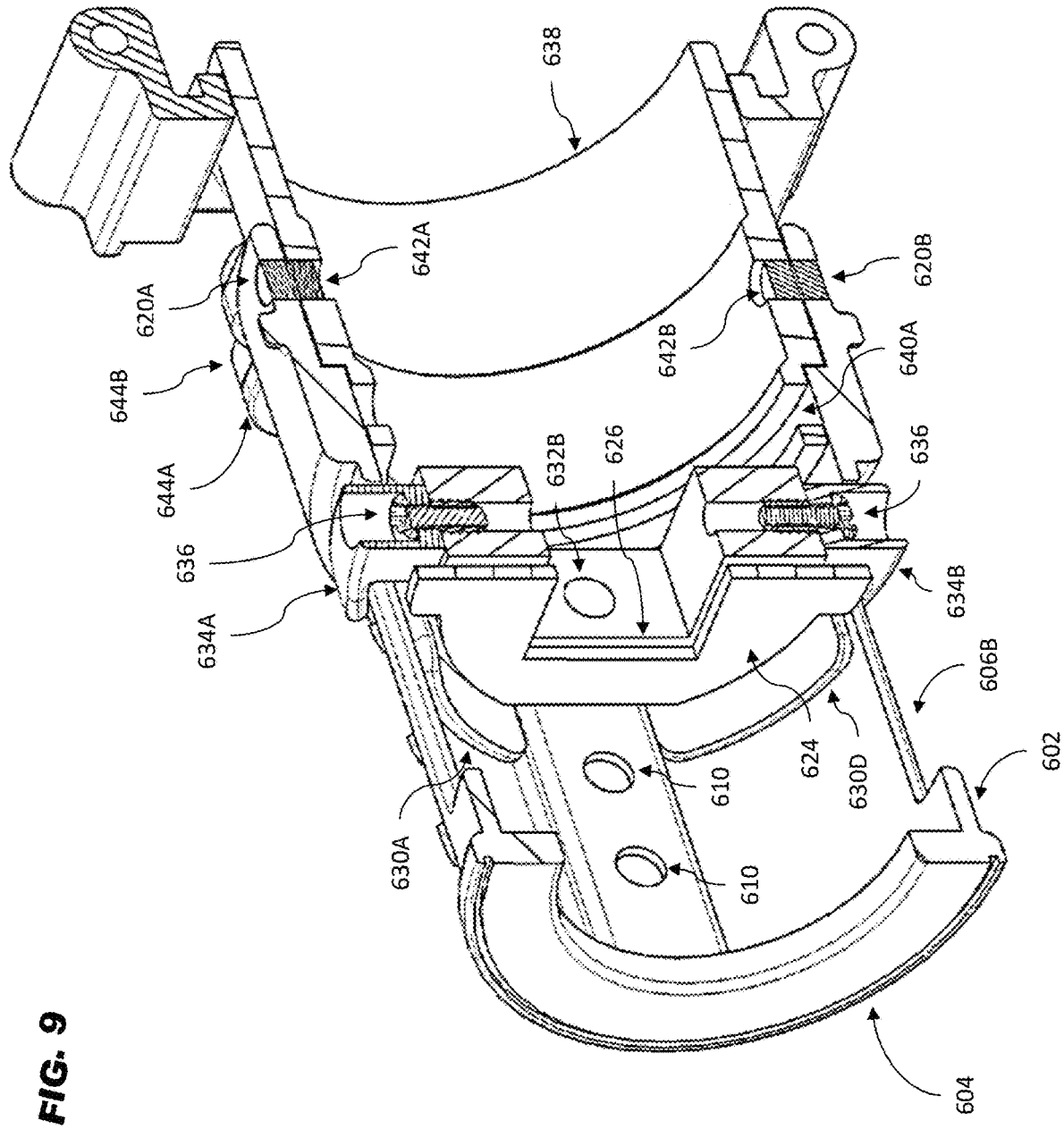
FIG. 9 is a sectional view from the same perspective as FIG. 8, but shows a collimator housing assembly, a collimator mount assembly, and a collimator chassis assembled together.

FIG. 8 is a sectional view rotated ninety degrees to the views in FIGS. 7A-C, showing the collimator mount assembly 520 at the Size-2 sensor position. FIG. 9 is a sectional view from the same perspective as FIG. 8, but shows the collimator housing assembly 510, collimator mount assembly 520, and collimator chassis 530 assembled together. As shown in FIG. 9, magnets 620A and 642A are proximate (i.e., positioned next to) each other and are attracted to each other thereby inhibiting rotation of the collimator housing assembly 510 relative to the collimator chassis 530. In a similar manner, magnets 620B and 642B are positioned next to each other and further inhibit rotation of the collimator housing assembly 510 relative to the collimator chassis 530.

Figure 10:
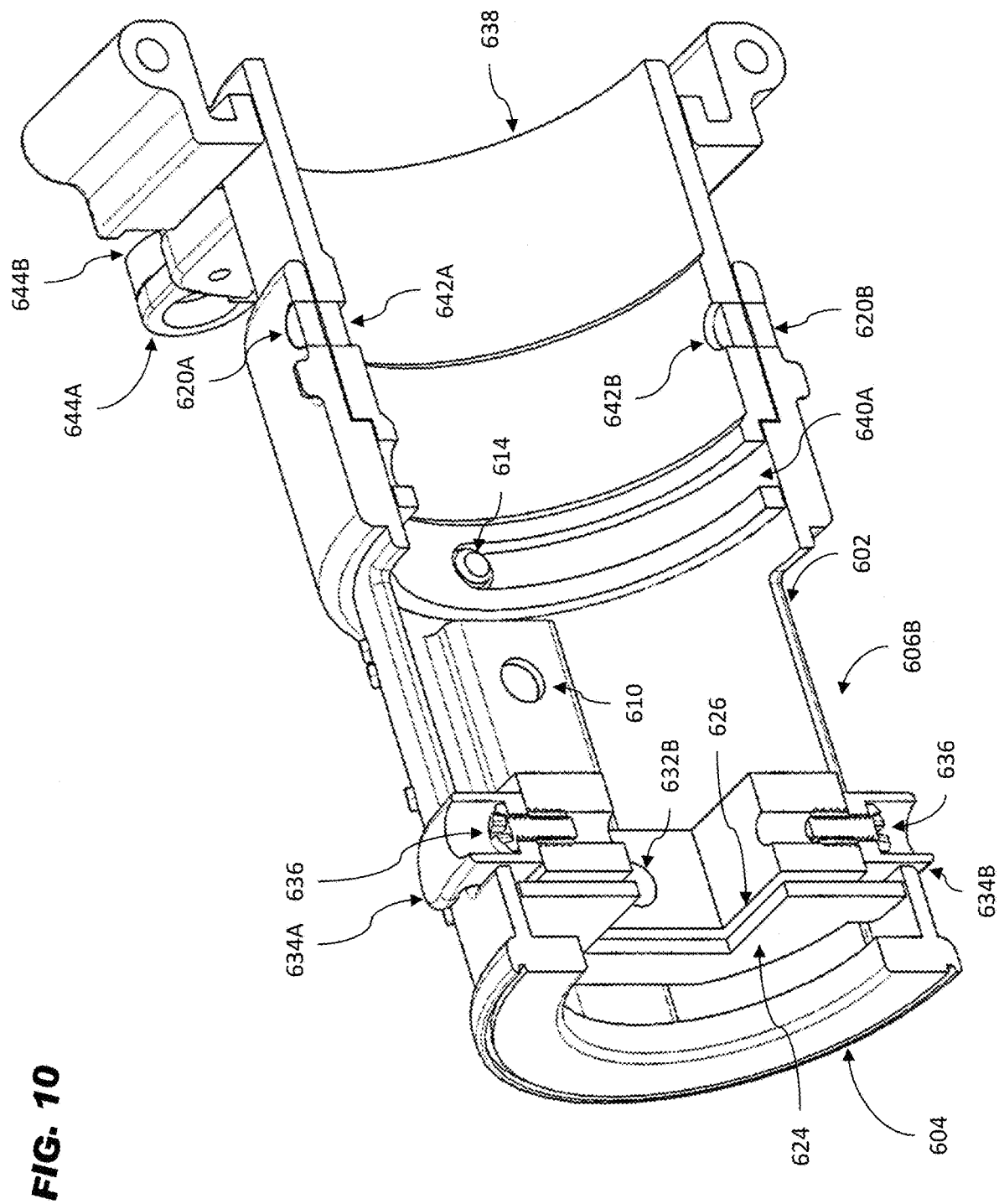
FIG. 10 is a sectional view of the collimation device according to one embodiment.

FIG. 10 is a sectional view that shows the collimator housing assembly 510, collimator mount assembly 520, and collimator chassis 530 assembled together. In FIG. 10, the collimator mount assembly 520 is at a position corresponding to the Size-0 intraoral sensor. As shown in FIG. 10, lock screw 614 protrudes into guide track 640A and is in contact with an end portion of guide track 640A. By such contact, the collimator housing assembly 510 is prevented from being rotated further in a counterclockwise direction.

Figure 11A:
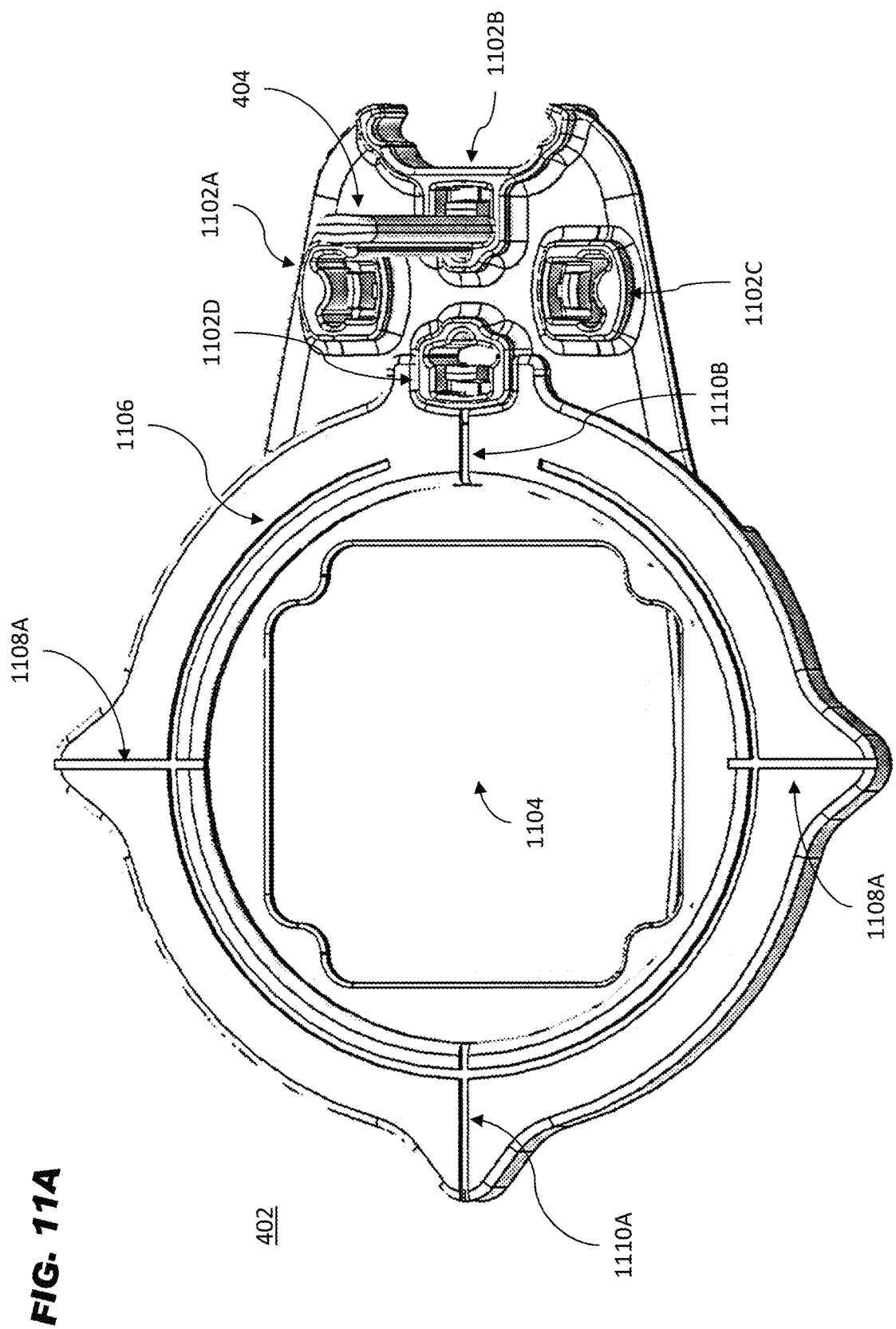
FIG. 11A is an illustration of alignment ring.

As discussed above, the x-ray sources 104/204 may be used in conjunction with an alignment device 400 that includes an alignment ring 402. FIG. 11A is an illustration of alignment ring 402. The alignment ring 402 is shown as generally circular, but may be of any shape. Alignment ring 402 is generally divided into the following items: a plurality of openings 1102A-D, a window opening 1104, a primary alignment groove 1106, vertical alignment grooves 1108A-B, and horizontal alignment grooves 1110A-B. The plurality of openings 1102A-D are constructed to receive a corresponding arm 404 of the alignment device 400. The arms 404 may, in one embodiment, have different cross-sectional profiles. Thus, each of the openings 1102A-D may have a different cross-sectional profile so as to match the arms 404. Each arm 404 may correspond to a particular type of radiographic image. For example, one arm 404, when used in a corresponding opening 1102A-D, may provide for a buccal image, whereas another arm 404, when used in its corresponding opening 1102A-D, may provide for a lingual image. Regardless of the type of radiographic image, each of the arms 404 are designed to position the intraoral sensor (x-ray detector 202), held by a holder at one end thereof, in the center of the window opening 1104.

In FIG. 11A, the primary alignment groove 1106 is shown as a C-shaped groove, but this is only exemplary. For example, the primary alignment groove 1106 could be a circle; specifically, a circle formed by connecting the distal ends of the C-shaped groove 1106 in FIG. 11A which are separated by horizontal alignment groove 1110B. The primary alignment groove 1106 may also be of another shape, for example: square, triangular, or a polygon. Preferably, the light emitting alignment device 604 projects a pattern that matches (or substantially matches) the shape of the primary alignment groove 1106. Thus, in the embodiment shown in FIG. 11A, the primary alignment groove 1106 is C-shaped substantially matching the pattern emitted by the light emitting alignment device 604.

The vertical alignment grooves 1108A-B and horizontal alignment grooves 1110A-B on the alignment ring 402 can also be used to determine proper alignment and position. Collimation device 500 may include additional light emitting alignment devices that project light onto the vertical and horizontal alignment grooves. In one embodiment, lasers 650A and 650B project laser beams that, if the x-ray source 104/204 and the x-ray detector 202 are properly aligned and positioned, are incident on horizontal grooves 1110A-B.

As discussed above, to ensure that the x-ray source 104/204 is properly aligned and at the proper distance from the x-ray detector 202, collimation device 500 is provided with a light emitting alignment device 604 that projects a light beam 1112 onto the alignment ring 402. The collimator is properly aligned when the light pattern falls within the targets on the aiming ring. As discussed above, in one embodiment, the light beam 1112 is circular. If the x-ray source 104/204 is properly positioned and aligned with respect to the alignment ring 402, the light beam 1112 emitted by the light emitting alignment device 604 will fall on the primary alignment groove 1106.

Figure 11B:
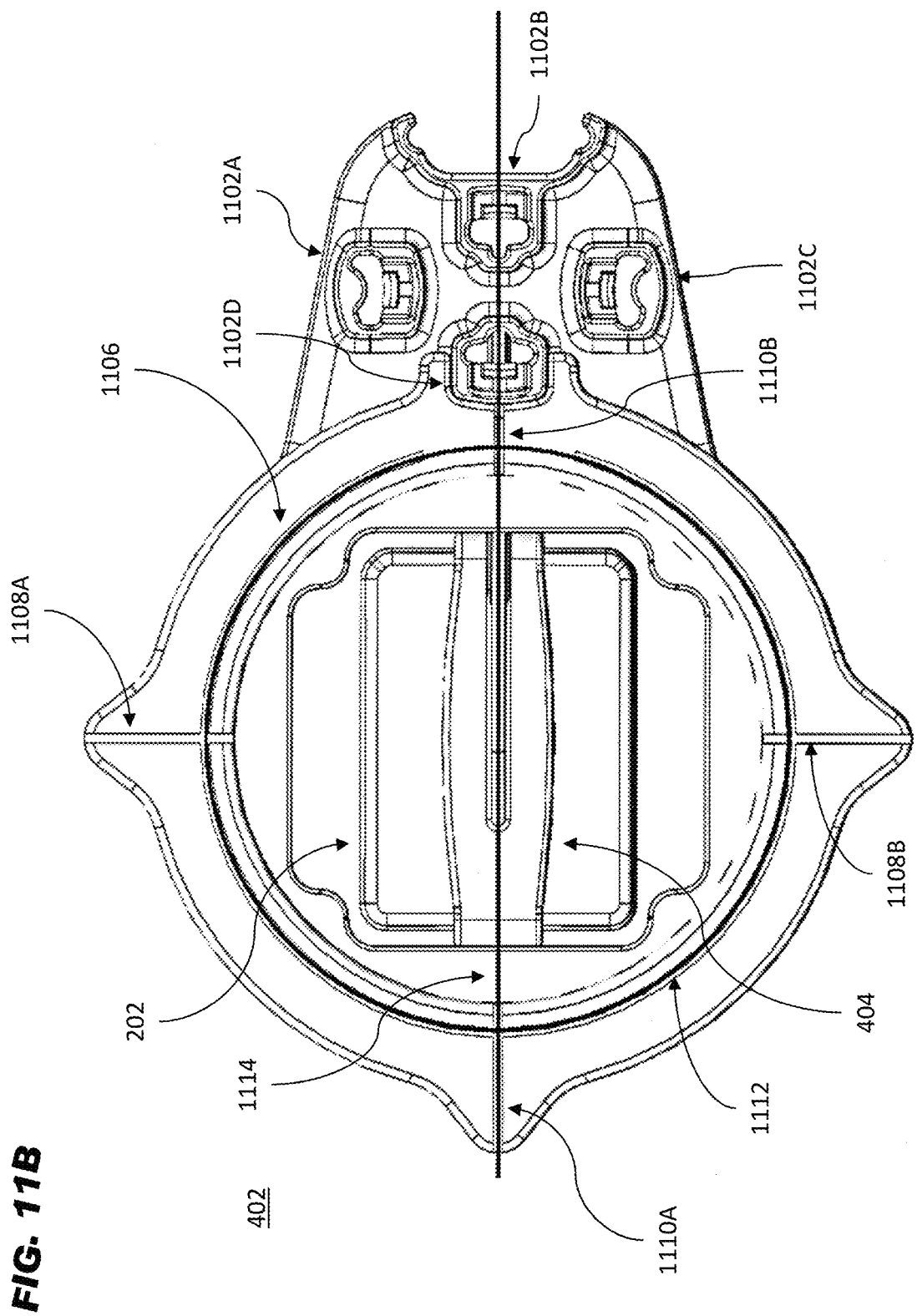
FIG. 11B illustrates a situation where an x-ray source is properly positioned and aligned with respect to an x-ray detector.

FIG. 11B illustrates a situation where the x-ray source 104/204 is properly positioned and aligned with respect to the x-ray detector 202. As shown in FIG. 11B, the circular light beam 1112 emitted from the light emitting alignment device 604 falls within the primary alignment groove 1106. In addition, laser light 1114 emitted from laser beams 650A and 650B fall within the horizontal alignment grooves 1110A-B. FIG. 11B also shows x-ray detector 202 (in the form of an intraoral sensor) held by a holder and centered in the window opening 1104.

Figure 11C:
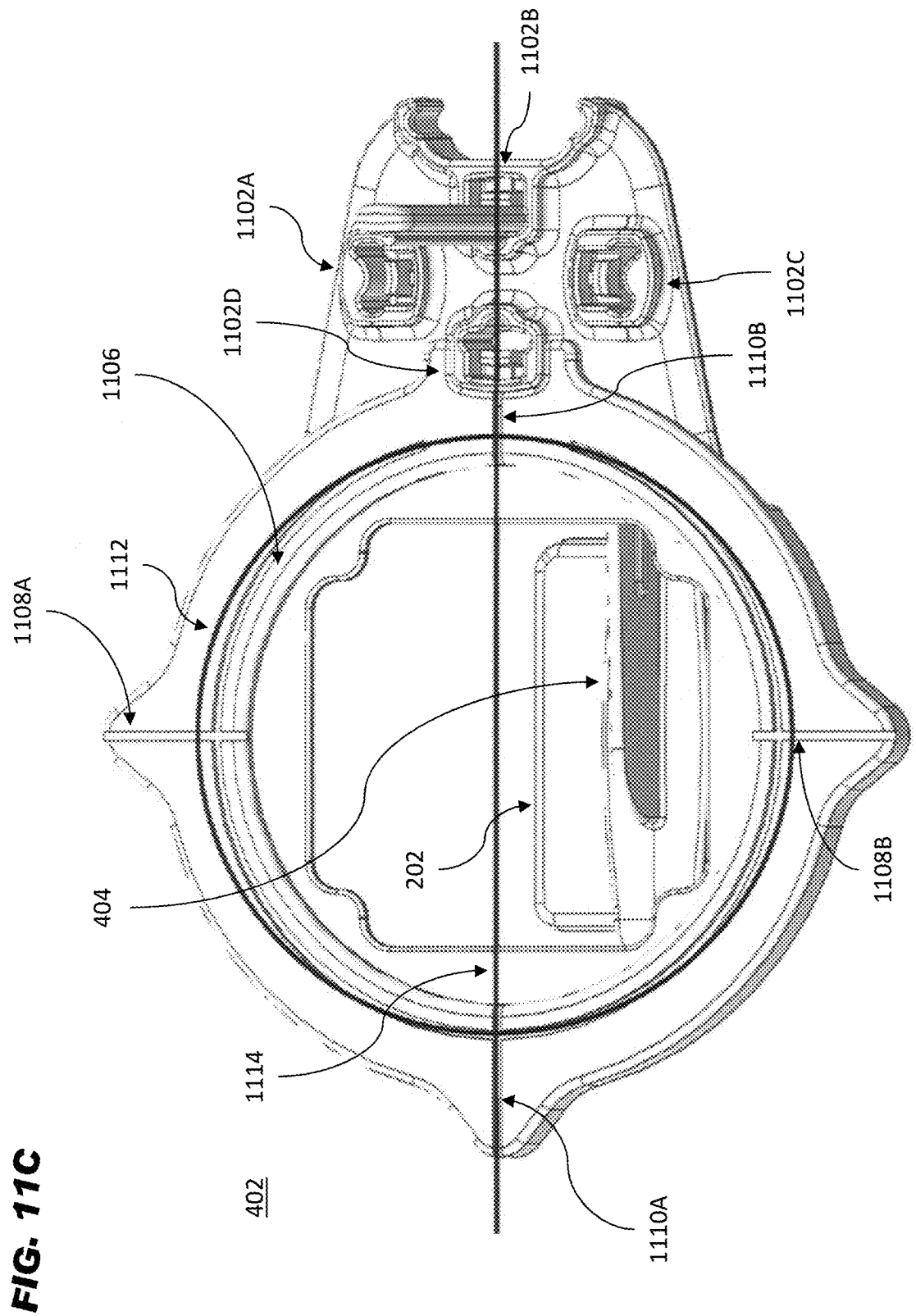
FIG. 11C illustrates a situation where an x-ray source is not properly positioned and aligned with respect to the x-ray detector.

FIG. 11C, however, illustrates a situation where the x-ray source 104/204 is not properly positioned and aligned with respect to the x-ray detector 202. As shown in FIG. 11C, the circular light beam 1112 emitted from the light emitting alignment device 604 falls, at least partially, outside of the primary alignment groove 1106, indicating that the x-ray source 104/204 is not properly positioned and/or aligned with respect to the x-ray detector 202. While the laser light 1114 emitted by laser beams 650A and 650B fall within the horizontal alignment grooves 1110A-B, that alone does not indicate a proper positioning and alignment, but rather only indicates that a corresponding axis is properly aligned. As discussed above, the light emitting alignment device 604 may also project a pair of parallel lines or four dots. The alignment ring 402 may include corresponding grooves (e.g., a pair of parallel grooves) or depressions (e.g., four depressions) on a side thereof. In the former case, if the pair of parallel lines is incident on the pair of parallel grooves, it indicates that the x-ray source 104/204 and the x-ray detector 202 are aligned in an XYZ coordinate system and that no yaw, pitch, or roll misalignments are present. Similarly, in the latter case, if the four dots fall within the four depressions, it indicates that the x-ray source 104/204 and the x-ray detector are aligned in an XYZ coordinate system and that no yaw, pitch, or roll misalignments are present.

With the features described above, an x-ray source may be provided with a collimation device 500 that it is adjustable depending on the size of the x-ray detector (e.g., an intraoral sensor) that is being used. The collimation device 500 aids in ensuring that x-rays emitted by the x-ray source are confined to a region of diagnostic interest. The collimation device 500 may be used in x-ray imaging (e.g. x-ray imaging system 100) or in a tomosynthesis imaging system 200. In addition, the collimation device 500 may be provided with a light emitting alignment device 604 that, when used in conjunction with alignment ring 402, may assist in ensuring proper positioning and alignment of the x-ray source and the x-ray detector.

The various embodiments described above have been presented by way of example and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present invention is sufficiently flexible and configurable, such that it can be utilized and navigated in ways other than that shown in the drawings.

Further, the purpose of the Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way. It is also to be understood that the procedures recited in the claims need not be performed in the order presented.

What is claimed is:

1. A collimation device for a dental imaging apparatus, the collimation device comprising:
    a collimator housing having a first end and a second end opposite to the first end, the collimator housing being configured to allow x-rays to move through the device in a direction from the first end to the second end; and
    a collimator plate constructed to at least partially block the passage of some of the x-rays moving through the device,
    wherein the collimator plate is movable relative to the collimator housing between a first position to a second position along the collimator housing, with the collimator plate being closer to the first end of the collimator housing when the collimator plate is in the first position than the collimator plate is to the first end of the collimator housing when the collimator plate is in the second position.

2. The collimation device of claim 1, wherein the collimator plate is movable to a third position between the first position and the second position.

3. The collimation device of claim 1, further comprising:
    a light emitting alignment device connected to the collimator housing and configured to generate a patterned light beam.

4. The collimation device of claim 1, further comprising:
    a collimator chassis,
    wherein the collimator housing is rotatably connected to the collimator chassis such that the collimator housing is rotatable between a first orientation and a second orientation.

5. The collimation device of claim 1, wherein an exterior surface of the collimator housing includes a first indicator indicating the first position and a second indicator indicating the second position.

6. The collimation device of claim 3, wherein the patterned light beam is a circular pattern.

7. The collimation device of claim 4, wherein the second orientation is ninety degrees from the first orientation.

8. The collimation device of claim 4, further comprising:
    a laser device connected to the collimator chassis and configured to emanate a laser beam.

9. The collimation device of claim 4, wherein the collimator housing includes a first pair of indexing elements and a second pair of indexing elements,
    wherein the collimator chassis includes a third pair of indexing elements,
    wherein the first pair of indexing elements are proximate to the third pair of indexing elements when the collimator housing and the collimator chassis are in the first orientation, and
    wherein the second pair of indexing elements are proximate to the third pair of indexing elements when the collimator housing and the collimator chassis are in the second orientation.

10. A collimation device for a dental imaging apparatus, the collimation device comprising:
    a collimator housing having a first end and a second end opposite to the first end, the collimator housing being configured to allow x-rays to move through the device in a direction from the first end to the second end;
    a collimator plate constructed to at least partially block the passage of some of the x-rays moving through the device; and
    a collimator mount assembly connected to the collimator plate,
    wherein the collimator housing includes a guide rail on which the collimator mount assembly is movable between a first position and a second position along the collimator housing, and
    wherein the collimator plate is closer to the first end of the collimator housing when the collimator plate is in the first position than the collimator plate is to the first end of the collimator housing when the collimator plate is in the second position.

11. An x-ray imaging system comprising:
    an x-ray source configured to generate an x-ray beam; and
    a collimation device connected to the x-ray source and arranged to receive the x-ray beam generated by the x-ray source, the collimation device including:
        a collimator housing having a first end and a second end opposite to the first end, the collimator housing being configured to allow x-rays of the x-ray beam to move through the device in a direction from the first end to the second end; and
        a collimator plate constructed to at least partially block the passage of some of the x-rays of the x-ray beam moving through the device, the collimator plate being movable relative to the collimator housing between a first position to a second position along the collimator housing, with the collimator plate being closer to the first end of the collimator housing when the collimator plate is in the first position than the collimator plate is to the first end of the collimator housing when the collimator plate is in the second position.

12. The x-ray imaging system of claim 11, wherein the collimator plate is movable to a third position between the first position and the second position.

13. The x-ray imaging system of claim 11, wherein the collimation device further comprises a light emitting alignment device connected to the collimator housing and configured to generate a patterned light beam in a direction of an aiming ring.

14. The x-ray imaging system of claim 11, wherein the collimation device further comprises:
   a collimator chassis,
   wherein the collimator housing is rotatably connected to the collimator chassis such that the collimator housing is rotatable between a first orientation and a second orientation.

15. The x-ray imaging system of claim 11, wherein an exterior surface of the collimator housing includes a first indicator indicating the first position and a second indicator indicating the second position.

16. The x-ray imaging system of claim 13, wherein the patterned light beam is a circular pattern.

17. The x-ray imaging system of claim 13, further comprising:
   an x-ray detector; and
   an alignment device that includes:
      a holder for holding the x-ray detector,
      an alignment ring, and
      a connecting arm connecting the holder to the alignment ring,
   wherein the alignment ring includes a primary alignment groove disposed on a side thereof, and
   wherein when the patterned light beam generated by the light emitting alignment device falls entirely within the primary alignment groove, the x-ray source is properly positioned and aligned relative to the x-ray detector.

18. The x-ray imaging system of claim 14, wherein the second orientation is ninety degrees from the first orientation.

19. The x-ray imaging system of claim 14, wherein the collimation device further comprises:
   a plurality of laser devices connected to the collimator chassis and configured to emanate respective laser beams.

20. The x-ray imaging system of claim 14,
   wherein the collimator housing includes a first pair of indexing elements and a second pair of indexing elements,
   wherein the collimator chassis includes a third pair of indexing elements,
   wherein the first pair of indexing elements are proximate to the third pair of indexing elements when the collimator housing and the collimator chassis are in the first orientation, and
   wherein the second pair of indexing elements are proximate to the third pair of indexing elements when the collimator housing and the collimator chassis are in the second orientation.

* * * * *